(12) United States Patent
Carr

(10) Patent No.: US 10,043,373 B2
(45) Date of Patent: Aug. 7, 2018

(54) SYSTEM FOR PROVIDING ADVANCE ALERTS

(71) Applicant: Mayhem Development, LLC, Lebanon, MO (US)

(72) Inventor: James Edward Carr, Lebanon, MO (US)

(73) Assignee: EmergencMe, LLC, Lebanon, MO (US)

( * ) Notice: Subject to any disclaimer, the term of this patent is extended or adjusted under 35 U.S.C. 154(b) by 0 days.

(21) Appl. No.: 15/151,442

(22) Filed: May 10, 2016

(65) Prior Publication Data

US 2016/0335879 A1 Nov. 17, 2016

Related U.S. Application Data

(60) Provisional application No. 62/159,942, filed on May 11, 2015, provisional application No. 62/190,449, filed on Jul. 9, 2015.

(51) Int. Cl.
*G08B 29/00* (2006.01)
*G08B 23/00* (2006.01)
(Continued)

(52) U.S. Cl.
CPC ....... *G08B 25/006* (2013.01); *G06F 19/3418* (2013.01); *G08B 25/005* (2013.01);
(Continued)

(58) Field of Classification Search
CPC .. G08B 15/002; G08B 25/005; G08B 25/008; G08B 25/014; G08B 25/14; G08B 27/001; G08B 7/066
(Continued)

(56) References Cited

U.S. PATENT DOCUMENTS

2006/0109113 A1* 5/2006 Reyes ............... G08B 7/06
340/541
2008/0175356 A1* 7/2008 Seidberg ............ G08B 25/08
379/45
(Continued)

OTHER PUBLICATIONS

"Smark911," Retrieved at: https://www.smart911.com/ on May 8, 2016, 4 pages.
(Continued)

*Primary Examiner* — Emily C Terrell

(57) ABSTRACT

Examples provide an advance alert system. Emergency data including medical information is collected from a set of subscribers and stored. On receiving a threat alert from a user, an alert generation component sends an alert notification, including a threat level, to the set of subscribers within an alert zone associated with a source of the threat alert. On receiving an imminent threat alert, a call to an emergency response system is automatically initiated. On receiving a request for access to the emergency data associated with the user from an emergency responder, a unique identifier for one or more emergency responders is checked to determine if the emergency responder is authorized to access the emergency data. If the emergency responder is authorized, access is granted and the emergency data is output to the emergency responder in an anonymous format. A notification of the emergency data access is sent to the user.

20 Claims, 20 Drawing Sheets

(51) Int. Cl.

| | |
|---|---|
| *G08B 25/00* | (2006.01) |
| *G08B 25/01* | (2006.01) |
| *G08B 27/00* | (2006.01) |
| *G06F 19/00* | (2018.01) |
| *H04W 4/021* | (2018.01) |
| *G16H 10/60* | (2018.01) |
| *H04W 4/90* | (2018.01) |
| *H04L 29/06* | (2006.01) |

(52) U.S. Cl.
CPC ......... *G08B 25/016* (2013.01); *G08B 27/005* (2013.01); *G16H 10/60* (2018.01); *H04L 63/10* (2013.01); *H04W 4/021* (2013.01); *H04W 4/90* (2018.02); *G08B 25/001* (2013.01); *H04L 63/08* (2013.01)

(58) Field of Classification Search
USPC .............................................. 340/506, 573.1
See application file for complete search history.

(56) References Cited

U.S. PATENT DOCUMENTS

| | | | |
|---|---|---|---|
| 2009/0045942 A1* | 2/2009 | Schurter | A62C 99/00 340/539.11 |
| 2012/0023592 A1* | 1/2012 | Wilson | G06F 19/323 726/28 |
| 2012/0123786 A1* | 5/2012 | Valin | G06Q 20/105 704/273 |
| 2013/0166323 A1* | 6/2013 | Heath | G06F 19/322 705/3 |
| 2014/0278664 A1* | 9/2014 | Loomis | G06Q 10/063118 705/7.17 |
| 2016/0148490 A1* | 5/2016 | Barnes | G08B 25/016 455/404.1 |

OTHER PUBLICATIONS

"Waze," Retrived at: https://www.waze.com/ on May 8, 2016, 4 pages.

\* cited by examiner

| NAME 1002 | HOH 1004 | GENDER 1006 | DOB 1008 | AGE 1010 | PHONE 1012 | EMAIL 1014 | LICENSE 1016 | NOTES 1018 | OPTIONS 1020 |
|---|---|---|---|---|---|---|---|---|---|
| NAME 1 | ✓ | M | 11/01/66 | 49 | (123)555-7890 | test@123 | ABC | DIABETIC | EDIT |
| NAME 2 | ✓ | F | 11/01/70 | 45 | (123)555-1234 | test@ABC | XYZ | DEAF | EDIT |
| NAME 3 | | M | 11/01/11 | 4 | | | | NONE | EDIT |

| USER DATA: 1102 | OUTPUT ANONYMOUS DATA: 1104 |
|---|---|
| • JOHN SMITH, MALE, HOH<br>• DOB-1/1/1975 | • MALE, HOH<br>• 37-41 YEARS OLD |
| • JUDY SMITH, FEMALE, HOH<br>• DOB-1/1/1980 | • FEMALE, HOH<br>• 32-37 YEARS OLD |
| • JOHN SMITH, JR., MALE<br>• DOB-1/1/1997 | • MALE<br>• 18 YEARS OLD |
| • SARA SMITH, FEMALE<br>• DOB-1/1/2002 | • YOUTH<br>• 13 YEARS OLD |

FIG. 11

SYSTEM FOR PROVIDING ADVANCE ALERTS

CROSS-REFERENCE TO RELATED APPLICATION

This application claims the benefit of U.S. Provisional Patent Application Ser. No. 62/159,942 entitled "Securely Providing Information to Emergency Responders", filed on May 11, 2015, and U.S. Provisional Patent Application Ser. No. 62/190,449 entitled "Multi-Stage System for Providing Advance Alerts", filed on Jul. 9, 2015, both of which are incorporated herein by reference in their entirety for all intents and purposes.

BACKGROUND

Providing for the safety of individuals who live or travel alone while also safeguarding their privacy is challenging. In particularly, the elderly or disabled often desire greater levels of autonomy than their family or caregivers feel is safe or prudent. Likewise, individuals frequently sense or become aware of a potential threat to their safety or potential medical problems before they arise. However, they are frequently unwilling to call for assistance due to fears of raising a false alarm, avoiding embarrassment, or wasting emergency services resources.

SUMMARY

Examples of the disclosure provide an advance alert system. An alert generation component sends an alert notification to a set of subscribers within an alert zone in response to receiving a threat alert from a user within the alert zone. An authorization component verifies a unique identifier associated with one or more emergency responders requesting access to emergency data associated with the user to determine if the one or more emergency responders are authorized. If the one or more emergency responders are authorized, a response component sends the emergency data to the one or more emergency responders.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 10 is an exemplary block diagram of a user data collection page.

FIG. 11 is an exemplary block diagram of generating anonymous data from user provided data.

Corresponding reference characters indicate corresponding parts throughout the drawings.

DETAILED DESCRIPTION

Figure 1:
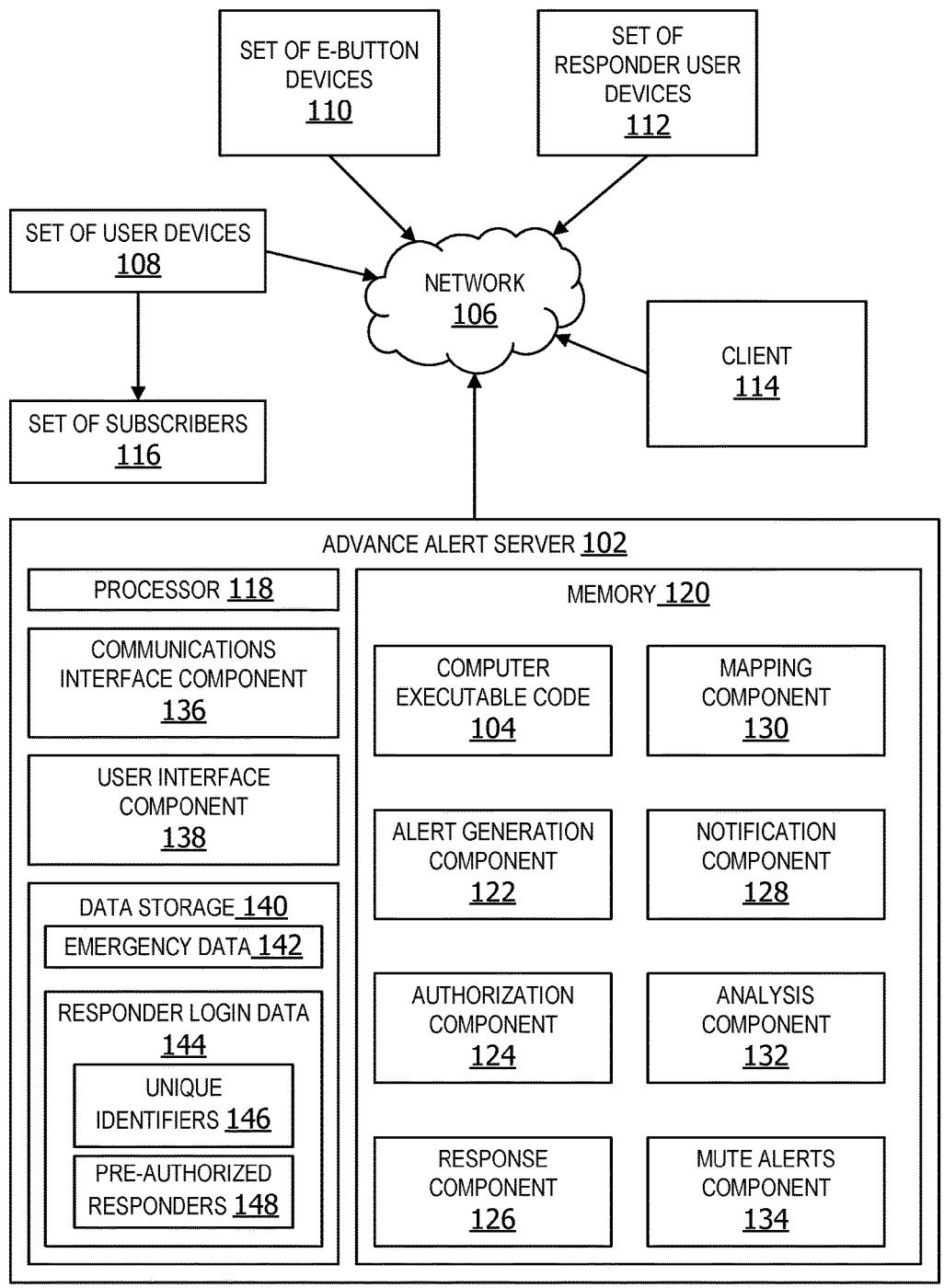
FIG. 1 is an exemplary block diagram illustrating an advance alert system environment.

Referring to the figures, examples of the disclosure enable a system for providing advance alerts and emergency data to users. In some examples, the advance alert system collects and stores emergency data for a plurality of users. In other words, the system records data that may be useful to emergency responders in the future. This recording of emergency data for later distribution to emergency personnel enables more efficient, accurate, and potentially life-saving responses from emergency responders.

In some examples, the system receives a request from a first emergency responder for access to a user's emergency data. Before providing the emergency data, the system requests an authorization from at least one authorized responder. In some examples, the authorization includes a valid login. The login includes an email, password, a quick authentication code, and/or a reason code. In some examples, a single user may provide the authorization to gain access to the information. In other examples, the login information is provided by two or more authorized users prior to the system providing the requested information to the at least one user requesting access to the information. This two-step authentication and reason code enables the system to provide emergency user data that is useful to emergency personnel for improving quality and accuracy of care and other emergency services provided to the user while safeguarding data security and preventing misuse of data by authorized parties.

In other examples, the emergency data provided to authorized emergency responders is anonymous emergency data. The anonymous emergency data is user data having unnecessary identifying information removed or replaced with generalized data that protects the anonymity of users. This feature enables emergency personnel to utilize the emergency data while protecting the privacy of the users.

In another example, the system provides a notification to the user and/or to a supervisor of the emergency responders accessing the user's emergency data. This notification ensures that the user is aware of every emergency responder that obtains access to the user's information. This feature limits any potential unauthorized accesses and enables a user to monitor accesses to their data for improved security and prevention of misuse by third parties.

In other examples, the notification component sends a notification to one or more of the user's designated emergency contact persons, such as family members, guardian, and/or head of household. For example, if the user is a minor, the notification is sent to the designated head of household, parent, guardian, or other pre-designated family member or emergency contact persons identified in the user's profile. The user's profile may be set to send the notification to the designated emergency contact persons located outside the alert zone if any threat alert is sent, regardless of the alert level.

The notification in some examples is sent to the designated emergency contact persons regardless of where the emergency contact person is within the alert zone or outside the alert zone. For example, but without limitation, if a minor child sends a yellow level threat alert, a notification is sent to the minor child's parent even if the parent is outside the alert zone. In another example, if a user initiates an imminent threat alert, a notification is sent to a spouse of the user even if the spouse is outside the alert zone.

In other examples, the notification is sent to one or more emergency contact person(s) only if the alert is at a pre-selected alert level. For example, a user may pre-select to send a notification to one or more emergency contact persons outside the alert zone only if the alert level is an imminent threat level but a notification is not sent to emergency contact person(s) outside the alert zone if the threat level is only a perceived threat level.

Likewise, a notification may be sent to a given user's emergency contact persons if a notification alert is received by a user device associated with the given user. For example, but without limitation, if a minor child's user device receives a notification of an imminent threat, weather alert, or other alert, a notification of the alert is sent to one or more user devices for one or more emergency contact persons, such as the child's parents. In this manner, a parent is notified of potentially hazardous conditions associated with a current location of their child, even if their child did not send or initiate a threat alert.

In another example, the system sends notification alerts to a set of subscribers in an alert zone in response to receiving a threat alert from one or more users in the alert zone. This feature provides improved access to emergency services, timely and effective interventions in potentially hazardous or life threatening situations, while warning other users in the vicinity of a health or safety issue of a potential problem prompting greater awareness or caution from the other users in the area. The alert notifications also reduce risk to other users in the area of a crime, natural disaster, fire, local flooding, or other hazardous situation by providing an advance warning to these other users that would otherwise be unaware of the potential danger.

In some examples, the threat alerts generated and sent by user devices decreases the response time of emergency responders coming to the aid of one or more users experiencing a medical, safety, or other issue. This decreased response time may save lives.

In still other examples, the notification sent to emergency responders includes an identification of active user devices within an alert zone, within a structure, within a car, or within another area. In some examples, if emergency responders are responding to a fire at a residence, the notification provided to authorized emergency responders includes an identification of user devices within the residence. The presence of user devices within the residence indicates a potential presence of a user within the residence. This information assists emergency responders in locating and rescuing people within the residence.

In still other examples, the emergency data provided to authorized emergency responders includes an identification of user devices within an alert zone and/or user devices within a structure, such as a home. This information assists emergency responders in locating and assisting people within the alert zone or within a structure.

Referring again to FIG. 1, an exemplary block diagram illustrates an advance alert system environment 100. In the example of FIG. 1, the advance alert server 102 represents a system for providing alert notifications and emergency data to authorized users. The server 102 represents any type of computing device executing computer executable code 104 (e.g., as application programs, operating system functionality, or both) to implement the operations and functionality associated with the server. The computer executable code 104 may also be referred to as computer executable instructions.

The server 102 sends data to one or more user devices and receives data from the one or more user devices via a network 106. The network 106 may be implemented via any type of network, including a wide area network (WAN), a local area network (LAN), wired, wireless, or any other type of network. In some examples, the network 106 connecting the advance alert server with the user devices includes BLUETOOTH, Wi-Fi, near field communication (NFC), cellular communications, or any other connection method. The term NFC as used herein refers, in some examples, to a short-range high frequency wireless communication technology for the exchange of data over short distances.

In this non-limiting example, the server 102 connects to a set of user devices 108, a set of e-button devices 110, a set of responder user devices 112, and a client 114 via the network. The set of user devices 108 is a set of one or more computing devices associated with one or more subscribers in a set of subscribers 116.

A user may include residents, employees, students, churchgoers, or any other individuals associated with a user device associated with an instance of the advance alert application. A subscriber may be a user receiving a notification or alert from the advance application server In general, a subscriber is a user associated with the advance alert system. A subscriber in some examples includes a user providing emergency data to the advance alert system. In other examples, a subscriber is a user having an account on the advance alert system including user data provided by the user. In still other examples, a subscriber is a user associated with a user device having an advance alert application capable of sending threat alerts to the server 102 or receiving threat notifications from the server 102.

A threat alert is an alert indicating a perceived threat. A user may initiate a threat alert having a user selected threat level when the user perceives a threat or potential threat. For example, a diabetic may be aware their blood sugar is low before any serious symptoms occur. Likewise, an individual may notice suspicious activity before a crime occurs.

In another example, a person may feel mild physical symptoms which cause apprehension of a possible medical problem before more serious symptoms manifest, but the person may be unwilling to call for medical assistance before the mild symptoms become more severe. In such cases, the person's symptoms may escalate so quickly they are unable to call for assistance.

In still other cases, one or more people may become aware of a hazardous condition in a given geographical area or region and wish to warn others of that condition. For example, a driver may encounter a disabled vehicle or jack-knifed semi-truck in the middle of a roadway. In another example, an individual may be aware of a grass fire, local flooding, icy roads, black ice, severe winds, hail, tornado touch down, an obstruction or debris in a roadway, a bridge out, heavy rains, a fallen tree, downed power line, deer crossing the road, animal in the road, snow, sleet, or any other hazardous condition in a particular area. The individual in these examples may initiate a threat alert to notify other subscribers within the alert zone of the potentially hazardous condition.

The set of e-button devices 110 is a set of one or more devices capable of sending data to the server 102 and receiving data from the server 102. An e-button device is a user device associated with a subscriber. An e-button device may be connected to a surface, such as a dash of a car, a console, a visor, or other surface in an automobile. The e-button device may also be coupled, taped, clipped, or attached to a wall, bed rail, wheel chair, walker, cane, belt, or any other surface for convenient access by a user. In other examples, the e-button device is implemented as a key chain e-button device.

The set of responder user devices 112 is a set of one or more computing devices associated with an emergency responder. An emergency responder is any type of emergency services or public services personnel. An emergency responder may include personnel, employees, or volunteers associated with an emergency service, medical provider, law enforcement, security services, or any other public or private agency, services, organization, or entity providing emergency response. An emergency response service may be a federal, state, or local response service. An emergency response service may include police department, fire department, volunteer fire department, ambulance service, park services, sheriff department, or any other emergency response service.

Examples of emergency responders include, without limitation, a 911 operator, an emergency medical technician (EMT), fire fighter, police officer, ambulance personnel, search and rescue personnel, coast guard personnel, disaster recovery personnel, health service personnel, medical personnel, public safety personnel, forest ranger, sheriff, deputy sheriff, marshal, security personnel, campus police office, life guard, or any other emergency services personnel.

A user device may include a mobile computing device or any other portable computing device executing the advance alert application. In some examples, the user device includes a mobile telephone, laptop, tablet, computing pad, netbook, gaming device, and/or portable media player. The user device may also include a wearable computing device, such as a fitness tracker, smart watch, or other wearable computing device.

The client 114 is a computing device capable of sending and receiving alerts, as well as sending and receiving emergency data. The client 114 in this example may be any type of computing device. In this example, the client 114 may include less portable computing devices, such as desktop personal computers, stand-alone kiosks, tabletop devices, industrial control devices, wireless charging stations, and electric automobile charging stations. The client 114 may also represent a computing device integrated into an automobile. Additionally, the computing device may represent a group of processing units or other computing devices.

In some examples, the server 102 has at least one processor 118, a memory 120. The processor 118 includes any quantity of processing units, and is programmed to execute computer executable code 104 for implementing aspects of the disclosure. The computer executable code 104 may be performed by the processor 118, by multiple processors within the computing device, or performed by a processor external to the server. In some examples, the processor 118 is programmed to execute instructions such as those illustrated in the figures (e.g., FIG. 15, FIG. 16, FIG. 17, FIG. 18, and FIG. 19).

In some examples, the processor represents an implementation of analog techniques to perform the operations described herein. For example, the operations may be performed by an analog computing device and/or a digital computing device.

The server 102 further has one or more computer readable media such as the memory 120. The memory 120 includes any quantity of media associated with or accessible by the computing device. The memory 120 may be internal to the server 102 (as shown in FIG. 1), external to the server (not shown), or both (not shown). In some examples, the memory 120 includes read-only memory and/or memory wired into an analog computing device.

The memory 120 stores, among other data, one or more applications. The applications, when executed by the processor, operate to perform functionality on the server 102. Exemplary applications include mail application programs, messaging programs, location-based services, search programs, and the like. The applications may communicate with counterpart applications or services, such as web services accessible via the network 106. For example, the applications may represent server-side services executing in a cloud.

The memory area further stores one or more computer-executable components. Exemplary components include an alert generation component 122, an authorization component 124 a response component 126, a notification component 128, a mapping component 130, an analysis component 132, and a mute alerts component 134.

In this example, the alert generation component 122 is executed by the processor 118 of the server 102 to cause the processor to send a notification alert to the set of users associated with an alert zone in response to receiving a threat alert from at least one user within the alert zone. A notification alert is an alert sent to one or more subscribers within an alert zone. The notification alert may include a sound alert, vibration, light, text message, email, flashing indicator lights, verbal message, graphics, images, mapping data, or any other data. The notification alert may be output as an audible sound recording, audio output, or other sound indicating the alert level. The notification may include changing tempo, volume, amplitude, or other auditory queues indicating changing threat levels.

In other examples, the notification alert may be output in a visual format, including icons, graphics, flashing icon, text, alphanumeric characters, symbols, maps, or projected image. In still other examples, a color is output to indicate the threat level associated with the current alert.

In some examples, the notifications include a status of the user device. Notifications may indicate the user device is charging, under power, not connected to a data source, not connected to a power source, charging but not attached to a smart device or network, or other status information.

In other examples, the notification alert includes a professional alert level. The professional alert level indicates that the notification alert is coming from professional or other public services personnel. This alert may be in the form of varying colors, text or different alert sound. When emergency responders initiate an alert that is sent to subscribers within the alert zone, the notification alert includes an indicator identifying the source of the alert as a professional or public services/emergency responder rather than another subscriber.

The authorization component 124 is executed by the processor 118 to cause the processor to verify a unique identifier associated with an emergency responder requesting access to emergency data associated with a user. The response component is executed by the processor 118 to cause the processor to send the emergency data to the emergency responder in response to verification of the unique identifier associated with the emergency responder.

In some examples, the authorization component 124 requests a valid user login from one or more users requesting access to emergency data associated with a user, such as a subscriber. The user login in some examples includes an email address and password. In other examples, the user login includes a user name and password. In still other examples, a valid user login includes an authorization code. An authorization code is a code assigned to a valid emergency responder or other user authorized to access emergency data. In still other examples, the valid user login includes an email, password, and authorization code.

The authorization component 124 in some examples requests a reason code from a user requesting access to emergency data. In some examples, the authorization component 124 requests the reason code with the valid login prior to granting access to emergency data. In other words, the requesting user provides the authorization code and reason code to the authorization component 124 prior to receiving any emergency data. In still other examples, the authorization component 124 requests the reason code after providing the emergency data to an authorized user. In these examples, the user provides the reason code to the authorization component while viewing the emergency data or at some point in time after receiving access to the emergency data. For example, the reason code may be requested by the authorization component and/or received from a user within twenty-four hours after access to the emergency data is provide, within twelve hours after providing access to the emergency data, within one hour of providing access to the emergency data, or the reason code may be requested while the requesting user is viewing the emergency data.

In some examples, the authorization component 124 requests an authorization component with the reason code either prior to outputting the emergency data, during output or viewing of the emergency data, or some pre-determined period of time after granting access to the emergency data. The reason code may be requested after some predetermined period of time to permit emergency responders to provide the additional reason code information after an emergency situation has been resolved. This enables emergency responders to focus on responding to an emergency situation and complete the authorization process after the emergency has passed to avoid distracting or slowing the requesting user's response time.

In other examples, the mapping component 130 is executed to cause the at least one processor to generate a map including a current location of one or more users, a representation of the alert zone, and a safe direction indicator away from the alert zone. The map is output to the one or more users with the alert notification. The current location of one or more users may include the current location of one or more subscribers, as well as the current location of one or more emergency responders.

In another example, the notification component 128 is executed to cause the at least one processor to send a notification of access to the emergency data by at least one emergency responder to the at least one user associated with the emergency data. The user associated with the emergency data is the user that provided the emergency data to the advanced alert system. The emergency data is data associated with the user, the user's family, the user's residence, the user's vehicle, or other personal data. The emergency data in some examples is filtered to generate anonymous emergency data. In this example, the anonymous emergency data is the data output to authorized emergency responders.

In still other examples, the mute alerts component is executed to cause the at least one processor to stop sending of alerts to the set of user devices 108, the set of e-button devices 110, and the set of subscribers 116 within a mute alerts zone for a predetermined period of time. The alerts are muted in response to a request to mute alerts by an authorized emergency responder. In some non-limiting examples, an emergency responder may wish to mute alerts in a given alert zone for a given time period to prevent users from warning other subscribers of a highway patrol officer position on a highway. The feature prevents users from utilizing the threat alerts to thwart law officers during normal traffic surveillance. The mute may be engaged by a dispatcher, officer, or other police personnel.

The analysis component 132 analyzes data associated with threat alerts, dates and times of alerts, alert frequencies, emergency data accesses, access reason codes, number of alerts received within an area, and so forth. The analysis data may be used to improve transportation safety. In other words, advance alert data may be used to show time, data, and location of accidents and other traffic related incidents. This data is analyzed by the analysis component to determine where and when traffic problems are occurring. This data may be used to solve problems and address traffic congestions and incidents where they occur most frequently.

In another example, surveys may be utilized to confirm reasons for alert activations. The analysis component analyzes the survey responses to determine if there is a pattern.

For example, the analysis component 132 may analyze data to determine that a series of alerts happen at a similar time and location due to deer crossing incidents. This additional information may be utilized to take preventive measures, such as erecting signs that alert drivers of the hazard at peak times or sending an alert notification to drivers within the area at the peak times as a pre-indicator. The notification may include a light up indicator light on the user device of subscribers within the notification zone.

The analysis component 132 in other examples analyzes threat alerts received from a plurality of users in a particular area. The location data received from the plurality of user devices may indicate that East bound traffic is still moving but West bound traffic is at a standstill because user devices associated with the West bound traffic lanes are not showing any movement or changes in location data. The analysis component determines there is an accident, traffic jam, obstruction, or other stoppage in the West bound traffic lane. This information regarding the West bound lane stoppage is forwarded to the appropriate response personnel to assist with the provision of emergency services. This additional alert information regarding the lane stoppage may also be provided to subscribers to assist them in avoiding the traffic jam.

In some examples, the server 102 includes a communications interface component 136. The communications interface component 136 includes a network interface card and/or computer-executable instructions (e.g., a driver) for operating the network interface card. Communication between the server 102 and other devices may occur using any protocol or mechanism over any wired or wireless connection. In some examples, the communications interface is operable with short range communication technologies such as by using NFC tags.

In some examples, the server 102 is a stand-alone computing device, such as a kiosk or computer terminal. In these examples, the server 102 may optionally be located within a hospital, at a residence, business, industrial complex, factory, office building, or any other location. In such examples, an emergency responder requests emergency data directly from the server kiosk or terminal and receives the emergency data from the kiosk or terminal without a network.

In some examples, the server 102 optionally includes a user interface component 138. The user interface component 138 includes a graphics card for displaying data to the user and receiving data from the user. The user, in this example, may include a subscriber or emergency responder. The user interface component 138 may also include computer-executable instructions (e.g., a driver) for operating the graphics card.

Further, the user interface component 138 may include a display (e.g., a touch screen display, projected display, or natural user interface) and/or computer-executable code (e.g., a driver) for operating the display. The user interface component 138 may also include one or more of the following to provide data to the user or receive data from the user: speakers, a sound card, a camera, a microphone, a vibration motor, one or more accelerometers, a BLUETOOTH brand communication module, global positioning system (GPS) hardware, networked smoke detector, networked thermostat, and/or a photoreceptive light sensor. For example, the user may input commands or manipulate data by moving the server 102 in a particular way.

In this example, the server 102 optionally includes data storage 140. The data storage 140 includes any type of data storage device, such as, but not limited to, a disk, a data storage array, a flash drive, or any other type of data storage. The data storage 140 in this example includes emergency data 142 and responder login data 144. The responder login data 144 includes unique identifiers 146 assigned to authorized responders and pre-authorized responders 148.

In still other examples, the server 102 includes additional applications utilized for managing alerts and emergency data. For example, the server 102 may include dispatch software, tracking software, firehouse services software, emergency medical services (EMS) software, or any other type of data.

In still other examples, a user carries identification, bracelet, necklace, key chain, indicator on a driver's license, or other identifier alerting emergency responders that the user is a subscriber for whom emergency data may be available from the advance alert system. In one non-limiting example, if a user is in a traffic accident, the emergency responder or dispatcher may check or run the user's vehicle license plate number through a database to determine the user is a subscriber for whom emergency data is available. In another example, the user's license plate information may include a sticker indicating the user is a subscriber of the system. In still another example, a sticker indicating the user is a subscriber of the advance alert system may be located on a bumper, windshield, or other area of a vehicle.

If an advance alert terminal is available, the emergency responders may obtain the emergency data for the user from the terminal or kiosk. If a terminal or kiosk is not available, the emergency responder may obtain the emergency data via a user device connecting remotely to the server through a network.

In some examples, the advance alert system is contained in a discrete module at a business, hospital, residence, or other location. Such a system may be connected externally through wireless networks or through local area network (LAN) lines. The system may be integrated in existing alarm systems. A stand-alone terminal may be accessible from the entrance of the home or business. Alternatively, the system may be entirely accessible through an advance alert application running on a user device accessed remotely via a network.

In still other examples, the server receives data from networked sensors, such as networked smoke detectors and/or networked thermostats. The smoke detectors, thermostats, and/or other sensors in these examples are installed within a structure or other location within an alert zone. During an active threat alert, the server receives data from the sensors, such as the thermostats and/or smoke detectors, to determine locations of fires, smoke, or other potential hazards within an alert zone. The data regarding the location of the possible fires, smoke, or other environmental conditions is provided to users and emergency responders in the alert zone. This environmental conditions data in other examples is provided with the emergency data provided to authorized emergency responders.

Figure 2:
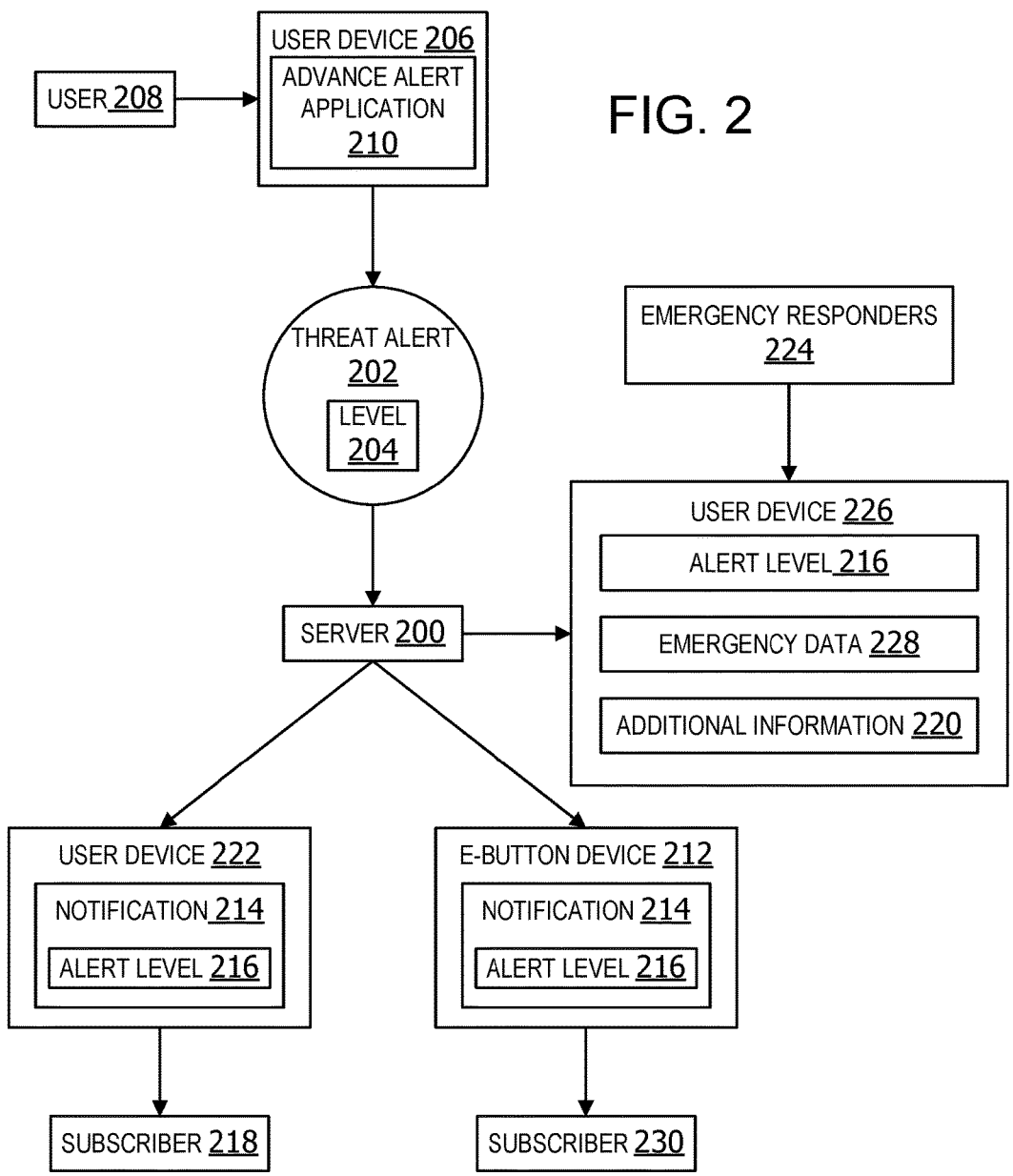
FIG. 2 is an exemplary block diagram of an advance alert system.

FIG. 2 is an exemplary block diagram of an advance alert system. The server 200 is an advance alert server, such as server 102 in FIG. 1. The server may be implemented as any type of computing device. In some examples, the server is a stand-alone computing device. In other examples, the server is a set of one or more servers. In still another example, the advance alert server is implemented as a cloud system.

In this example, the server 200 receives a threat alert 202 including a user-selected, threat level 204 from a user device 206. The user device 206 is any type of computing device associated with a user 208, such as a user device in the set of user devices 108 in FIG. 1.

The user device 206 in this example is running an advance alert application 210. The advance alert application 210 is an application that may be implemented on any mobile user device, such as cellular telephones, smart phones, communication devices, health monitoring device, such as wearable or accessory user devices. A health monitor is a device for monitoring health and/or vital signs of a user, such as heart rate, blood pressure, temperature, blood oxygen levels, etc. Non-limiting examples of wearable or accessory user devices include smart watches, glasses, pedometers, health monitors, headsets, earphones, wristbands, or other wearable devices.

The advance alert application 210 generates the threat alert and sends the threat alert to the server 102. The alerts are scaling alerts including different threat levels to indicate different threat levels. For example, a normal level, indicates there are currently no perceived threats reported in the immediate area or selected alert zone.

In other examples, if no perceived threat alert is reported or any received threat alerts are canceled or unverified the threat level is designated as the normal threat level. The normal level in other examples may also indicate that the hardware and/or software associated with the user device and/or e-button are functioning normally. In other words, in some examples, the normal level indicates no alerts, the user is logged into the system, and the system is active.

In some non-limiting examples, a threat level is indicated using one or more pre-determined color indicators. A normal level in some examples is indicated by a blue status, blue level, or blue color status indicator. In other examples, the normal level is identified by a green status, green level, or green color status indicator. The normal level in still other examples may be indicated by a white color, blue-green color, blue color, green color, or any other selected color to indicate a normal status.

In still other examples, the first threat level or perceived threat level is indicated by a yellow color indicator. In still other non-limiting examples, an imminent threat alert is indicated by a red color indicator. In other examples, an imminent threat level is indicated by a black color indicator, an orange color indicator, or any other color indicator for identifying an imminent threat. In other examples, an alert associated with construction is indicated by an orange color indicator.

In still other examples, the threat level is indicated using text or a symbol. For example, a normal level may be indicated by a green checkmark symbol, a yellow smiling face symbol, text of the word "normal", text of the word "green", or any other text or symbol designated to indicate a normal level.

The threat alert 202 at a first level 204 indicates a perceived threat. The perceived threat level may be referred to as a yellow alert, a caution alert, an awareness level 2, a warning level, yellow level alert, or increased awareness level. The perceived threat level is a second level within the escalating threat levels. This warning level indicates at least one user within the geographic area or selected zone has reported or initiated a perceived threat alert. Heightened awareness or caution by subscribers within the zone is appropriate.

In other examples, the threat alert 202 may be an alert including second level indicating an imminent threat. An imminent threat level alert may be referred to as a red alert, a danger alert, emergency alert level, or red level. The imminent threat level indicates a hazard, danger, threat, or medical emergency is imminent. Heightened awareness or greater caution is appropriate. In some examples, an imminent threat alert prompts the user device 206 to automatically initiate a 911 call if the user device 206 includes a cellular telephone or BLUETOOTH capability for making phone calls.

In some examples, initiating an imminent threat level triggers an automatic call to emergency services, such as, but not limited to, a 911 call, a call to a fire department, call to a police department, or other emergency services. In other examples, the system automatically forwards emergency data to the emergency responders responding to the call for emergency services.

In other examples, a call to emergency services is not made unless a user explicitly selects an emergency call level. The emergency call level is an optional emergency call option within the multi-level alerts. At the emergency call level, the user device automatically calls an emergency service if it is capable of doing so. In other examples, the advance alert server initiates the call to the emergency services. In some non-limiting examples, the advance alert server initiates the call to emergency services if a user device is incapable of making phone calls or unable to do so because of a lack of cell reception or low battery.

In this example, there are four threat levels. The levels include the normal level, the perceived threat level, the imminent threat level, and the emergency call level. In some examples, the user selects each of the threat level incrementally, beginning with level 1, then level 2, followed by level 3, and finally level 4. In this case, the user cannot reach level 4 without activating level 1, level 2, and level 3 in that order. In order to reach level 4, the user pushes the level selection button four times to reach the threat alert at level 4.

In other examples, the user may select any of these four different threat levels at any time rather than progressively moving through each of the various threat levels before reaching the desired threat level. In other words, the user may go from the normal level to the imminent threat level with a single selection.

In still other examples, if a user initiates the perceived threat level or the imminent threat level, the system waits a predetermined threshold wait time for a user to input additional data. The additional input may be an alert cancellation or selection of a different threat level. If the user fails to enter any additional input, the system prompts the user to enter input. If the user fails to enter any additional input for the threshold time, the system automatically upgrades the alert level to the emergency call level and makes the call to emergency services.

In still other examples, as the threat alert level increases, the alert zone radius also increases. In other words, when a threat alert level changes from a perceived threat to an emergency call level threat, the advance alert system automatically increases the radius and area covered by the alert zone, thereby increasing the number of subscribers receiving the alert notifications. Likewise, as an alert level decreases from a higher alert to a lower alert, the alert zone also decreases. When an alert is canceled and there are no other threat alerts originating within the alert zone, the alert zone is also canceled.

In another example, the threat levels only include two levels, the normal level and the imminent threat level. In this example, whenever a user initiates a threat alert, the alert is always at the imminent threat level. The advance alert system receiving the alert automatically sends a notification to subscribers within the alert zone and automatically notifies emergency services and/or one or more emergency responders.

In some examples, a user selecting a perceived threat level or an imminent threat level on the user device may initiate an alarm sound generate by the user device, a burglar alarm in a home, a car alarm on a vehicle, hazard lights on a vehicle, or other visual or auditory alarm which may bring assistance to the user.

A threat may include a hazardous condition, suspicious activity, possible criminal activity, a medical problem, physical discomfort, a potential medical problem, an injury, an accident, suspicious activity by another person, flooding, a storm, weather condition, an obstruction on a road, deer on a road, possible home invasion, or any other threat, hazard, emergency or situation which may indicate an increased level of caution or awareness.

For example, a notification alert may prompt a driver of a vehicle to slow down, stop, turn off a radio, pull over to the side of the road, take a freeway exit or choose an alternate route, make a U-turn, or just increase their awareness of their surroundings.

In another example, a user walking when they receive a notification alert may choose to walk in well-lit areas only, move indoors, go to a storm shelter, check the news on a mobile device, or simply be more aware of their immediate surroundings.

In still another example, a residence of an apartment building receiving a notification alert may be prompted to take a variety of actions, depending on the circumstances, such as remain indoors, leave the residence and go to a storm shelter, check on their neighbor, check the news, or simply be more aware of their surroundings.

On receiving the threat alert, the server 200 generates a notification alert 214 including the alert level 216. The server sends this notification alert to a user device associated with each subscriber located within an alert zone. In this example, the notification alert 214 is sent to e-button device 212 associated with subscriber 230 and user device 222 associated with subscriber 218.

In some examples, the notification 214 is sent to one or more user devices associated with emergency responders within the alert zone. In this example, the notification is a notification alert sent to user device 226 associated with emergency responder 224. The notification alert sent to the emergency responder 224 may include emergency data 228 and any available additional information 220 associated with the user 208 that initiated the original threat alert 202.

The additional information 220 in this example includes a location of the user device that sent the alert, a number of threat alerts received within the alert zone, the level of the received alerts, and any information derived from the alert data received from the user devices, surveys, or other information sources, such as road obstructions, weather conditions, etc.

Figure 3:
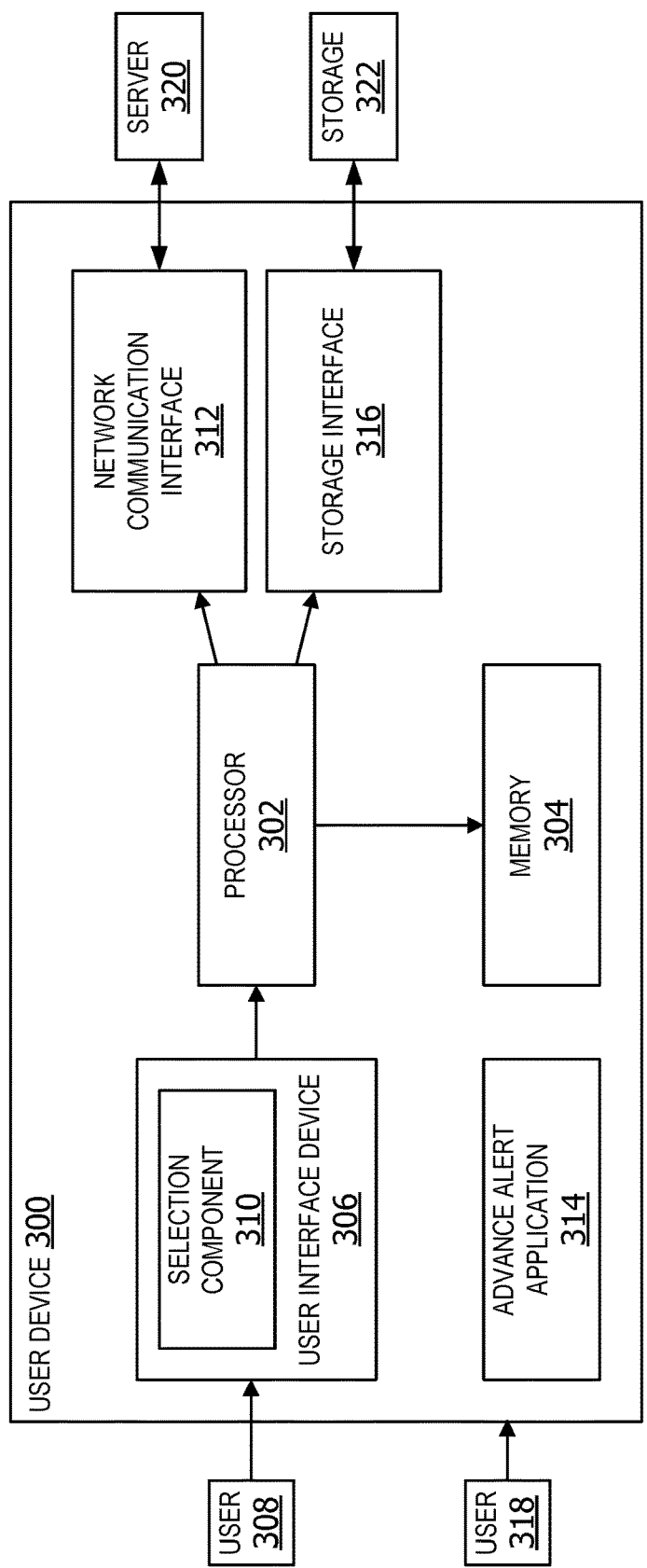
FIG. 3 is an exemplary block diagram of a user device for sending and receiving advance alerts and emergency data.

Referring now to FIG. 3, an exemplary block diagram of a user device for sending and receiving advance alerts and emergency data is shown. The user device 300 is a computing device associated with a user or emergency responder.

The user device 300 is a device for sending multi-level alerts and receiving multi-level alert notifications from the server. The user device 300 in this example includes hardware and software features. For example, the user device 300 in this non-limiting example includes at least one processor 302, a memory 304, and a user interface 306. The user 308 utilizes the user device 300 to send and receive alerts and notifications from the advance alert system. The user 308 enters data and views data via the user interface 306.

The user device 300 in this non-limiting example includes a network communication interface 312 for connecting to the server 320 via a network connection. The user device sends data to the server and receives data from the server via the network in this example. However, in other examples, the server is a kiosk or other stand-alone terminal. In these examples, the user enters data directly into a user interface of the server and receives data output by the server via the user interface of the server without a transmitting data over a network.

The user device includes software components, such as the advance alert application 314 and storage interface 316. The advance alert application 314 sends threat alerts to the server and receives threat notifications from the server. The advance alert application 314 in other examples provides a user login enabling a user to log into the server system and update a user profile, update emergency information associated with the user or the user's family members that is stored on the data storage 322, and view data access history for the user's data.

In some examples, the user interface 306 includes a selection component 310. The selection component 310 provides an interface for the user 310 to select an alert level. The user initiates a threat alert by selecting a perceived level of threat associated with the user device. The user interface 310 may include one or more icons on a graphical user interface (GUI), items in a menu, or other selector for choosing an alert level. In this example, the selection component 310 is provided within a graphical user interface (GUI). The e-button may be presented to the user on a physical display screen or within a projected image.

The user device 300 and corresponding advance alert application 314 receives input from the user in any way, including, but without limitation, from input devices such as a keyboard, toggle switch, button, pointing device, pressure sensor, or light sensor. In some examples, the user input is received via gesture input, touch screen, proximity input (such as by hovering), pointing device, audio input, voice input, or other input associated with the user device.

The user device 300 may also receive input from one or more other input devices, such as, but without limitation, video cameras, speakers, audio sensors, orientation sensors, pressure sensors, GPS sensors, and/or temperature sensors. The user device 300 may also optionally receive input from one or more peripheral or external devices.

In another example, user 308 and user 318 are emergency responders. In this example, both of the users 308 and 318 provide authorized user logins. When both users are verified as authorized responders, the server 320 provides access to the emergency data stored on the storage 322.

Figure 4:
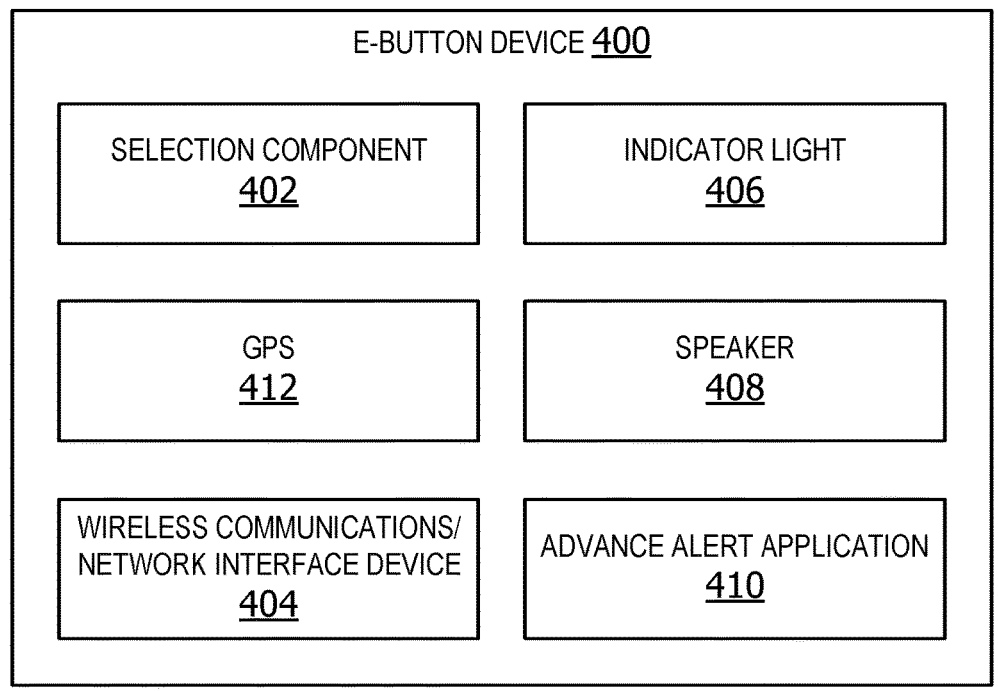
FIG. 4 is an exemplary block diagram of an e-button device.

FIG. 4 is an exemplary block diagram of an e-button device. An e-button device is a user device associated with a user or subscriber. The e-button is a hardware device including an advance alert software component. In this non-limiting example, the e-button includes a selection component 402, wireless communications/network interface device 404, indicator light 406, speaker 408, advance alert application 410, and a global positioning system (GPS) 412.

In this example, the selection component 402 is a physical component located on the e-button device 400, such as a physical button, switch, know, toggle, or other controller. In some examples, the threat alert is activated by pushing, pressing, flipping, sliding, turning, or pressing the selection component 402.

In some examples, the selection component 402 permits a user to initiate a threat alert at a user selected level. The user pushes the physical button to initiate a threat alert and select a perceived threat level. In one example, when a user presses or activates the e-button to initiate a particular threat level, notifications are sent to subscribers and/or responders within the selected zone associated with the user or user device that initiated the alert. Further pressing the e-button initiates a call to emergency services. The advance alert system opens a microphone and speaker on the user device for hands free usage during the emergency call and provision of information to emergency services personnel.

In another example, if the user device or e-button does not include a communications device, such as a cellular telephone, capable of making calls and/or sending texts, the advance alert application triggers a communications device external to the user device to initiate the call to the emergency services. In one example, the advance alert server makes the call to the emergency services on behalf of the subscriber/user if the user device is incapable of making the call.

The indicator light 406 includes one or more lights located on the e-button device. One or more lights light up to indicate an incoming notification alert and/or indicate the alert level. For example, a first level alert may be output to the user by turning on a yellow light on the e-button. In another example, an orange light indicates an alert associated with a construction zone. In still another example, a red light, a flashing red light, or a flashing light indicates an imminent threat level. A light is a type of visual alert which may be provided to users. A visual alert may be provided to hearing impaired users in some non-limiting examples.

The speaker 408 includes one or more speakers for playing an audio notification alert. An audio alert may include an alarm sound, a verbal alert including spoken words, as well as any other sound to indicate the alarm level. An audio alert may be provided to users who are blind or visually impaired. In other examples, an audio alert may be provided to users that are driving a vehicle or otherwise unable to look at a visual display.

The GPS 412 provides location data for the location of the user. In other examples, the GPS 412 provides location data to the server. The server uses this location data to determine a source of a threat alert, a location of the user sending the original threat alert, and/or the location of one or more subscribers. This location data is utilized by the server in some examples to select an alert zone radius from the source of the alert to a perimeter of the alert zone.

In some examples, the e-button device 400 is a hand-held or wearable device, such as a smart watch or other wearable computing device. For example, but without limitation, the e-button may be mounted to or integrated within a vehicle, such as a vehicle dash, console, radio, or other integrated device within the vehicle or vehicle bed.

The e-button may be integrated within or attached to a wheel chair, motorized scooter, or other computing device, such as a vehicle navigation system, home monitoring system, portable gaming console, programmable consumer electronics, and the like. In other examples, the e-button may be a separate, non-integrated device that may be attached to a surface within a structure, vehicle, or other structure. For example, the e-button may be attached to a surface within the vehicle, such as a windshield, dash, headliner, sun visor, cup holder, console, or other surface of the vehicle.

In one example, if the e-button is integrated within a vehicle, selecting a perceived threat level may automatically activate the vehicle hazard light system or the car alarm system. In other examples, activating the perceived threat level may initiate an audible alarm by the e-button or other user device generating the threat alert.

In still another example, an emergency vehicle equipped with the advance alert application automatically sends a notification alert to the set of subscribers within the alert zone in response to the emergency vehicle sirens being activated. In other words, when the sirens or emergency lights on an ambulance, police car, fire truck, or other emergency vehicle are turned on, the advance alert application running on a computing device of the emergency vehicle automatically sends an advance alert to a group of subscribers in the alert zone.

In another example, when an emergency vehicle turns on the siren and/or emergency lights, the advance alert application running on the user device associated with the emergency vehicle sends an alert to the server. The server determines an alert zone and sends an alert notification to the subscribers within the alert zone associated with the emergency vehicle. The alert notification may include an indication that the alert is from an emergency services provided or other professional.

In still another example, an emergency responder, such as a police officer or ambulance driver activates an alert on a user device or the emergency vehicle to send an alert to the server. The server determines an alert zone and sends an alert notification to the subscribers within the alert zone associated with the emergency vehicle. The alert notification may include an indication that the alert is from an emergency services provided or other professional. In another example, the alert notification may include an indication that the alert originated from an emergency vehicle, such as a police car, fire truck, ambulance, or other emergency vehicle.

The e-button device 400 may be wired or wireless, battery operated, or coupled with other devices, such as one or more universal serial bus (USB) or other appropriate port. The E-button may be powered directly, such as powered through a cigarette adapter, battery powered, or any other power source. If the e-button device 400 is battery powered, the batteries may be rechargeable or otherwise replaceable.

In some examples, the e-button device 400 is hardwired into an existing electrical power system in an automobile or other power supply. The e-button may be integrated with a device that has data access. The e-button device 400 may be plugged into a vehicle on-board diagnostics (OBD) port. The e-button device 400 in other examples may completely contain its connectivity and power system as a stand-alone device.

The e-button device 400 may accept input from the user in any way, including, but without limitation, from input devices such as a keyboard, toggle switch, button, pointing device, pressure sensor, or light sensor. In some examples, the user input is received via gesture input, touch screen, proximity input (such as by hovering), pointing device, audio input, voice input, or other input associated with the user device. For example, the e-button may include an audio/speech recognition feature which enables the user to activate the e-button or otherwise initiate a threat level alert using human speech or other audio input/output.

In some examples, the e-button is disabled while a vehicle or user associated with the e-button is moving or traveling at a pre-determined speed. When the user or vehicle speed indicates the user is not moving or moving at a speed that is below a threshold speed, the e-button re-activates.

In other examples, a built-in sensor dims/brightens an indicator light on the e-button depending on ambient light. A buzzer or chime may be included to note any escalation or increasing threat level alerts received.

Figure 5:
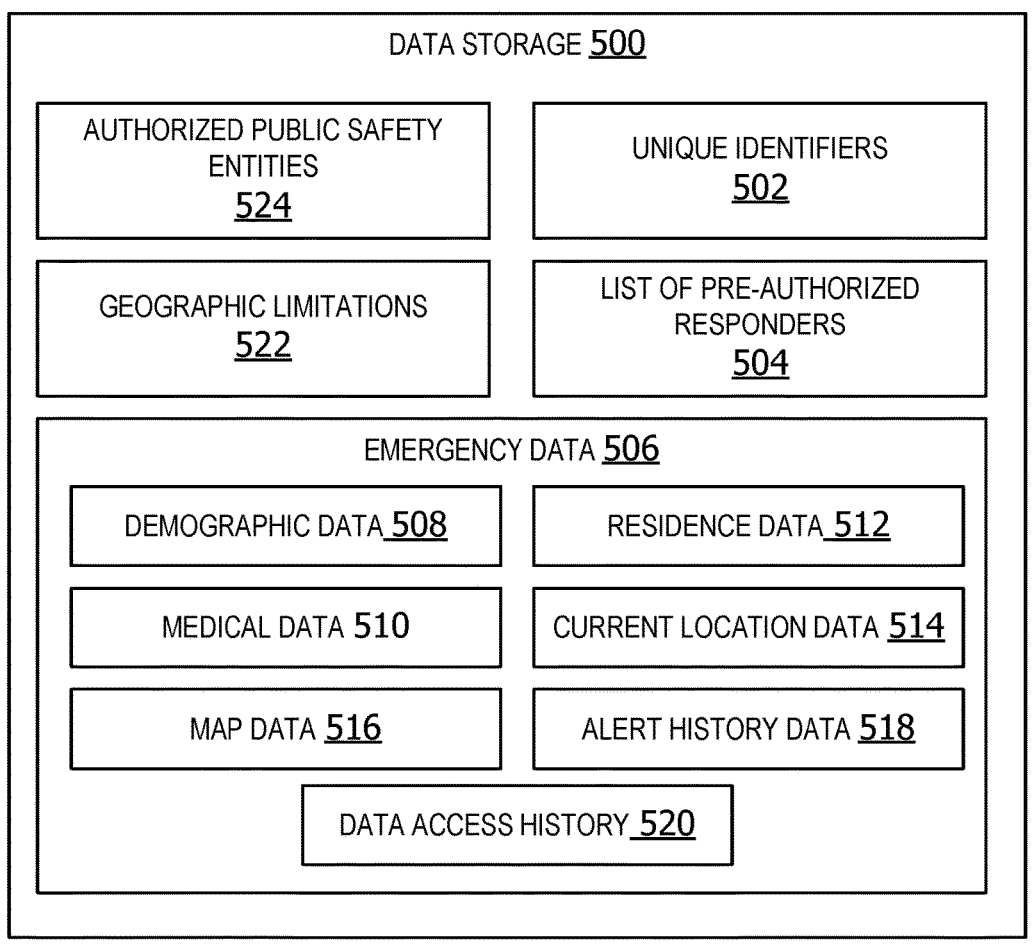
FIG. 5 is an exemplary block diagram of a data storage storing emergency data.

FIG. 5 is an exemplary block diagram of a data storage storing emergency data. The data storage 500 may be implemented as any type of data storage device. The data storage device may include a database for storing data. In other non-limiting examples, the data storage 500 is cloud storage accessible to the advance alert server via the network.

The data storage 500 stores unique identifiers 502 for emergency responders. The list of pre-approved responders 504 is a list of responders that have been pre-approved to access the user's emergency data. The list of pre-approved responders 508 may be a list or responders approved by the user.

In some examples, a user creates the list of pre-approved responders, such as, for example, family members, primary care physicians, and other known caretakers. Pre-approved responders in some examples are allowed to access the emergency data more quickly or by an alternative method, such as using biometrics. Biometrics may include voiceprint or thumbprint scan. Pre-approved responders in some examples are able to access the emergency data individually without a valid second emergency responder login.

The emergency data 506 is data provided by a user. The emergency data 506 includes demographic data 508, such as names and ages of users and other members of the user's household. The residence data 512 is data describing the house, apartment, or other residence of the user. The residence data 512 includes an address, type of dwelling, number of levels, whether there is an attic, basement, pool, storm cellar, garage, and other information describing the residence. The residence data 512 may also include a set of images of the residence overlaid with a set of markers identifying features of potential interest.

Medical data 510 includes information associated with a user. In some examples, the medial data 510 includes information indicating whether a user is non-ambulatory, sight impaired, hearing impaired, or other disabilities. In other examples, the medical data 510 optionally includes the user's current medical conditions, medications, dosages, medical care provider names, previous injuries, previous surgeries, and any other relevant medical information provided by the user. Medical data 510 may include locations where medications are usually taken, therapies, disabilities, pacemakers or other medical devices used, as well as known allergies. The medical data 510 may identify medical conditions such as hypertension, diabetes, pregnancy, heart conditions, diseases, previous illnesses, and any other medical information.

The current location data 514 is data identifying a current location of the user or user device associated with the user. The map data 516 includes mapping data describing locations of subscribers and locations of alert zones. This data may also include the user's usual location within a residence, such as bedroom, favorite room, favorite chair, etc.

The alert history data 518 is a record of threat alerts received from users within a particular geographic area over a given period of time. The alert history data 518 may include information associated with the identity of the user initiating the alert, the reason the user initiated the threat alert, the date and time the user initiated the threat alert.

The data access history 520 includes a history of emergency data accesses by emergency responders. The alert history data 518 may include names/identities of emergency responders accessing the user's emergency data, dates and times of emergency data accesses, and reason codes for accessing the emergency data.

In some examples, emergency responders may create accounts to authorize emergency responders through their line of work or affiliation with a particular organization or entity. For instance, an EMT may access the system independently and verify their employment with an ambulance company and create a login which is verified in advance and re-usable. Organizations which regularly employ emergency responders may have accounts with access to the system, enabling them to create and update emergency responder lists, and generate unique login codes for each employee. In some examples, the codes are not alphanumerical. Instead, the codes are radio frequency identifier (RFID) chips, barcodes, electronic keys, or other forms of portable keys which may be contained on an ID card, bracelet, chip, or other item.

The authorized public safety entities 524 in this example are a list of approved emergency responder organizations. Approved organizations are groups, agencies, entities, or organizations that are authorized to access user emergency data. For example, an authorized public safety entity may include an ambulance service, police department, fire department, etc. Employees of the authorized public safety entities may be authorized through their employment or affiliation with the authorized public safety entity, enabling them to create a unique login code for the system.

The geographic limitations 522 are user specified limitations applied to emergency responders requesting access to emergency data. Geographic limitations 522 may include limitations by state, by county, by city, or any other geographic limitation. For example, if a user lives in Texas, the geographic limitations may specify that only emergency responders in the state of Texas are permitted to access the user's emergency data. If an emergency responder from another state attempts to access the user's emergency data, the emergency responder request is denied based on the geographic limitations set by the user. Thus, only an authorized responder within the appropriate geographic area is permitted to access the emergency data.

In some examples, the emergency data may also include data gathered from a medical device or health/fitness device that monitors heart rate, number of steps taken, blood pressure, sleep cycles, or other information.

Figure 6:
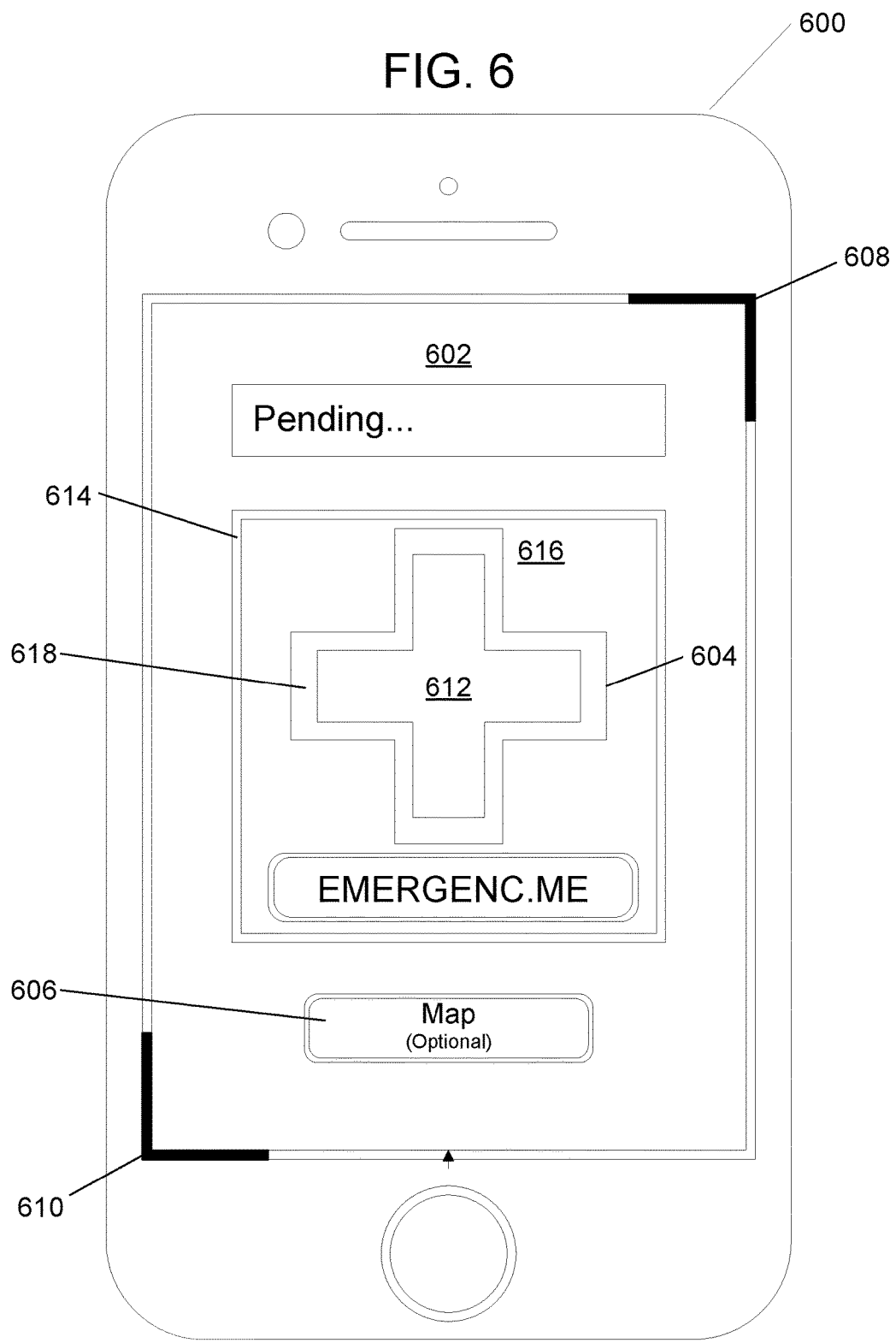
FIG. 6 is an exemplary block diagram of a user device for sending a threat alert or receiving a notification alert.

FIG. 6 is an exemplary block diagram of a user device 600 for sending a threat alert or receiving a notification alert. In this example, the user device includes a touch screen 602 displaying a graphical e-button 604. The user presses or touches the e-button 604 to activate a threat alert.

In some example, an area 612 on the interior of the e-button 604 indicates the user sent a threat alert or indicates a threat alert notification received by the user device. A threat alert notification indicates the threat alert was initiated by a different user.

The map icon 606 is a selection component for viewing a map. The user presses or touches the map icon 606 to view a map. The map may include the user's current location, a representation of the alert zone, an indication of the alert level, and/or an alert band, arrow or other indicator recommending a direction of travel away from the source of the threat alert and out of the alert zone. In some examples, the user device utilizes a compass of the mobile device to generate the map.

In other examples, the alert notification is displayed on a response screen of the user device. If the alert level is a first alert level, the alert notification is displayed with a color. In one example, the notification of a first alert level is displayed at least in part in a yellow color. In other non-limiting examples, if the alert is a second alert level, the alert notification is displayed on the screen 602 with a red color or a flashing red color.

The user device 600 in some examples displays an alert band 608 and alert band 610 at the perimeter of the touch screen. In this example, one alert band is a warning alert band and the other alert band is a recommended direction alert band. The warning alert band indicates a direction towards an origin of a threat alert, a location of a potential danger, or a direction of a center of an alert zone. The recommended direction alert band indicates a direction leading out of the alert zone, away from an origin of a threat alert, or a direction leading away from a location of a potential danger.

In this non-limiting example, the alert band 608 is a warning alert band indicating which direction the threat alert was sent from or the direction of a known hazard. The alert band 608 may optionally include a color indicator, such as, but not limited to, a red alert band. The alert band 610 in this example is a recommended direction alert band. The alert band 610 may include a color indicator, such as, but not limited to, a green alert band pointing to a direction away from the origination point of the threat alert or away from the location of a potential threat.

In other examples, the alert band 608 may be the recommended direction alert band and alert band 610 may be the warning alert band. Likewise, in this example, the alert band 608 is located in an upper right corner of the screen 602. However, in other examples, the alert band 608 may be located in the upper left hand corner, the lower left hand corner, the lower right hand corner, an upper portion of the touch screen, a lower portion of the touch screen, a central part of the touch screen, or anywhere else on the touch screen to indicate a direction going toward an origin of a threat alert or a direction away from an origin of a threat alert. In still other examples, but without limitation, an alert band is displayed around a portion of a perimeter 614 surrounding the graphical e-button 604, displayed within an area 616 surrounding the e-button, displayed around a portion of a perimeter 618 of the e-button itself, or provided via a compass type display on the screen.

In one non-limiting example, if a threat alert is initiated by a security team and indicates an active shooter at a particular location within an alert zone, the alert band 608 points toward the likely location of the shooter and the alert band 610 points to a direction most likely to lead away from the shooter or away from the potential danger.

In this manner, the user device 600 in some examples provides the user with a way to look at the touch screen 602 to determine a current threat level, whether the user initiated the threat alert or a threat notification was received indicating that someone else initiated a threat alert, which direction the threat originated from, and a recommended direction for the user to move away from the origination point of the threat alert or move out of the alert zone. This provides a quick indicator of which direction a user may go to avoid the potential danger without looking at a map.

In this example, the user device 600 displays two alert bands, a warning alert band and a recommended direction alert band 608. In other examples, the user device only provides a warning alert band indicating an origination point of the threat alert. In still other example, the user device provides only a recommended direction alert band.

In one example, the response screen includes a blue color indicating the advance alert system is active, the user is logged in, and/or any auxiliary devices are connected and operating normally. In another example, a yellow color on the response screen indicates an increased state of awareness. Examples might include animals in the roadway, emergency vehicles, etc.

In still another example, the response screen includes a flashing red color indicating an emergency. When selected, a 911 call is made with the user's device. The speaker is automatically turned on for ease of use.

In another example, the subscribers receiving a flashing red notification alert are alerted to an even higher state of emergency as someone has actually made a 911 call from the alert zone. In other examples, if multiple users within the alert zone initiate an imminent threat alert, the server automatically initiates the call to the emergency services based on the number of imminent threat alerts being sent within the same alert zone.

In yet another example, an orange color notification alert indicates an alert initiated by appropriate authorities to indicate construction is taking place. The construction notification alert is sent to one or more subscribers within a construction alert zone.

In still other examples, a notification alert may be sent by the appropriate authorities, public safety officials, or other authorized responders to alert subscribers of potential terror attacks, amber alerts associated with missing children, severe weather alerts, and other safety related conditions.

Figure 7:
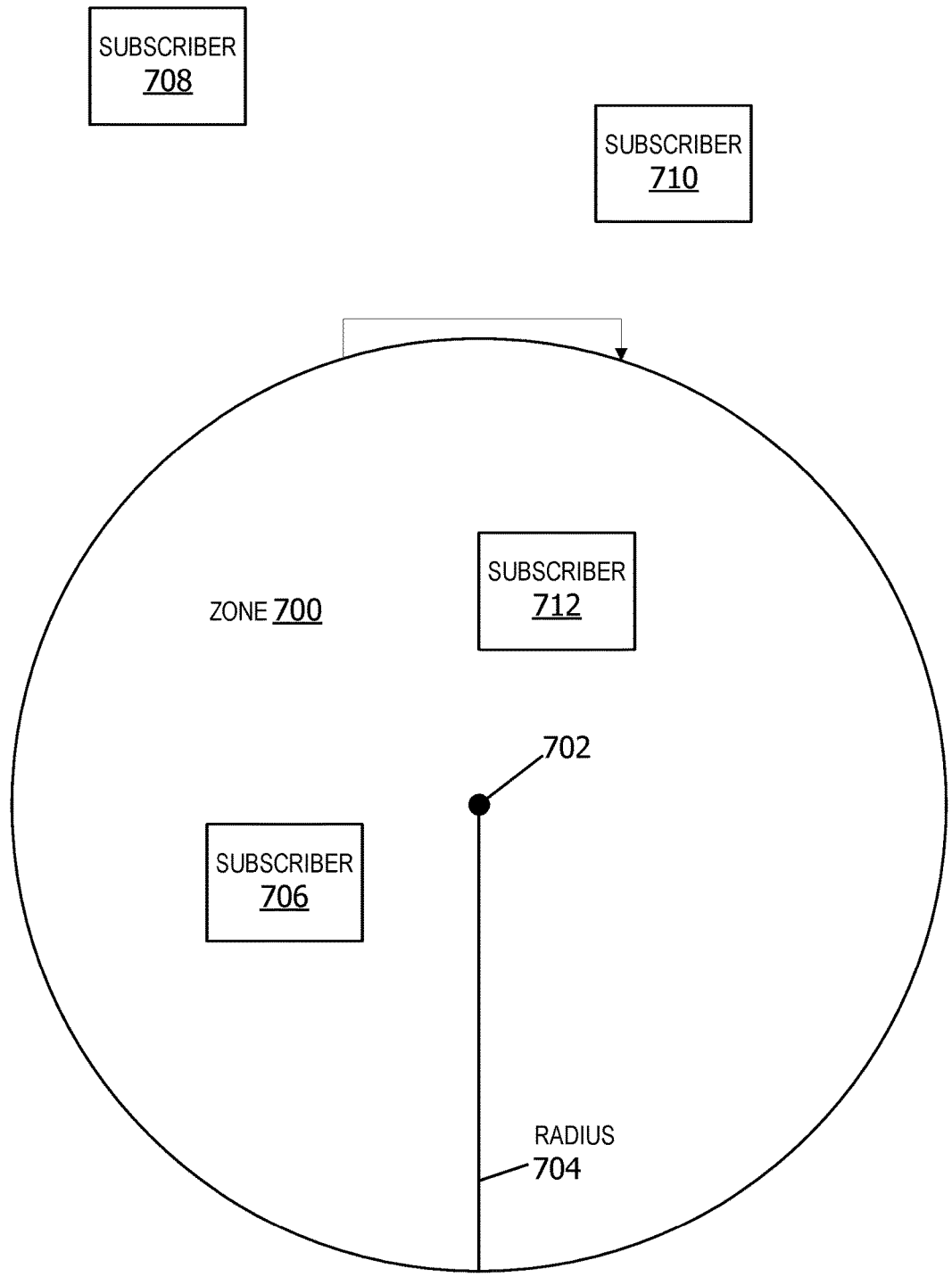
FIG. 7 is an exemplary block diagram of an alert zone associated with a set of subscribers.

FIG. 7 is an exemplary block diagram of an alert zone associated with a set of subscribers. An alert zone 700 is a zone associated with a source 702 of at least one threat alert. The alert zone 700 is a geographic region or area surrounding a location of the user sending the threat alert and/or the source of the threat alert.

The alert zone 700 has a radius 704. The radius is calculated based on the source 702 of the threat alert, the speed at which the user initiating the threat alert is moving, and any other factors associated with the geographic area. Non-limiting examples of factors include freeways, high crime areas, known hazards, number of alerts received in this area in the past, the current threat level, number of threat alerts being received from different users within the same area and the same time period, as well as any other factors.

A notification alert is sent to subscribers 706 and 712 within the alert zone. In this example, the notification alert is not sent to subscribers 708 and 710 because subscribers 708 and 710 are located outside the alert zone. In other examples, if subscriber 708 is a designated emergency contact of one or more users within the alert zone 700, the notification alert is also sent to the subscriber 708 outside the alert zone.

Figure 8:
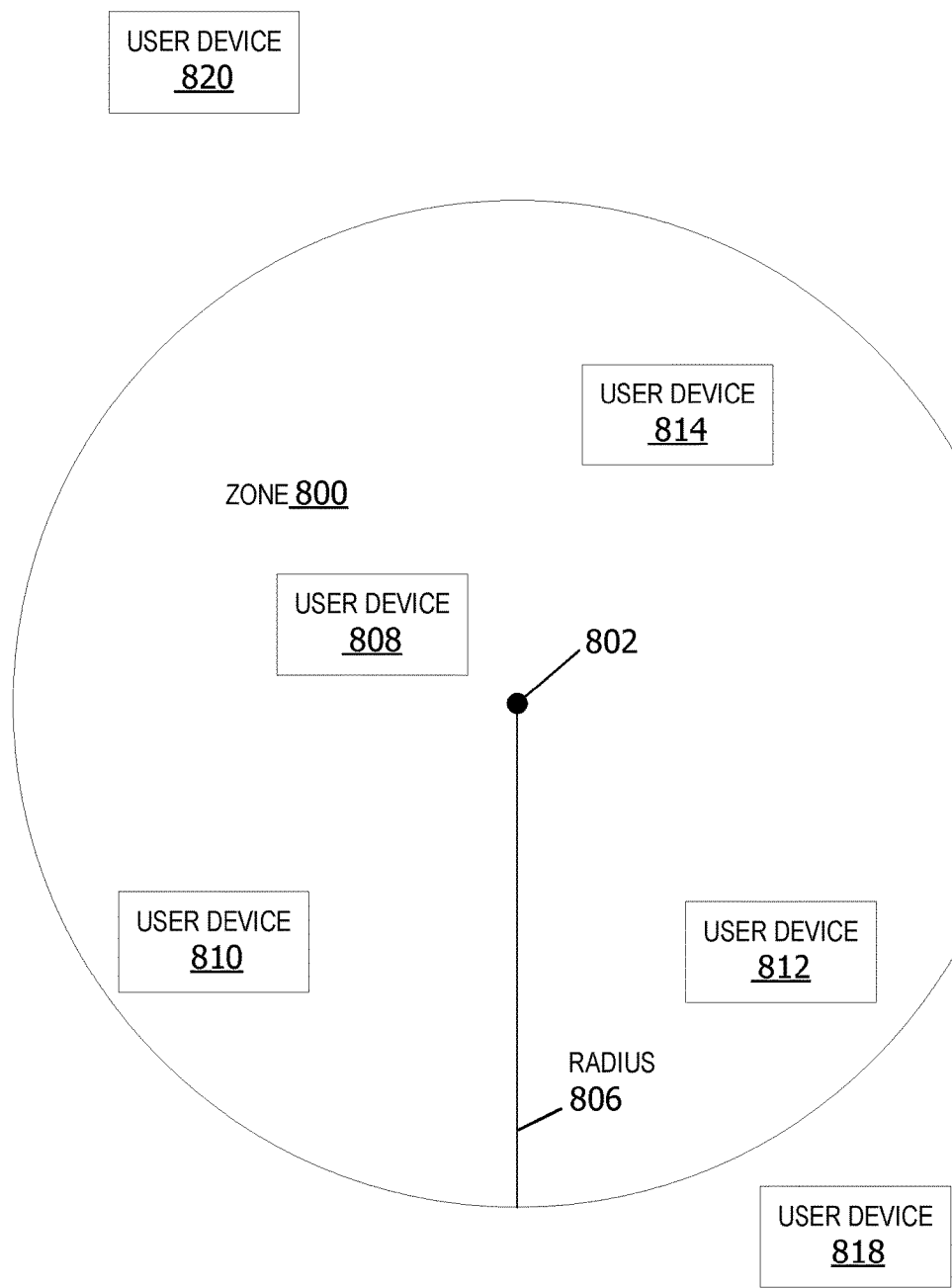
FIG. 8 is an exemplary block diagram of an alert zone associated with a set of user devices.

FIG. 8 is an exemplary block diagram of an alert zone associated with a set of user devices. The alert zone 800 is a zone or area including a location 802 of the user initiating the threat alert and having a radius 806. The advance alert system sends an alert to user devices 808, 810, 812, and 814 within the alert zone. The advance alert server does not send an alert notification to user devices 818 and 820 located outside the alert zone 800.

Figure 9:
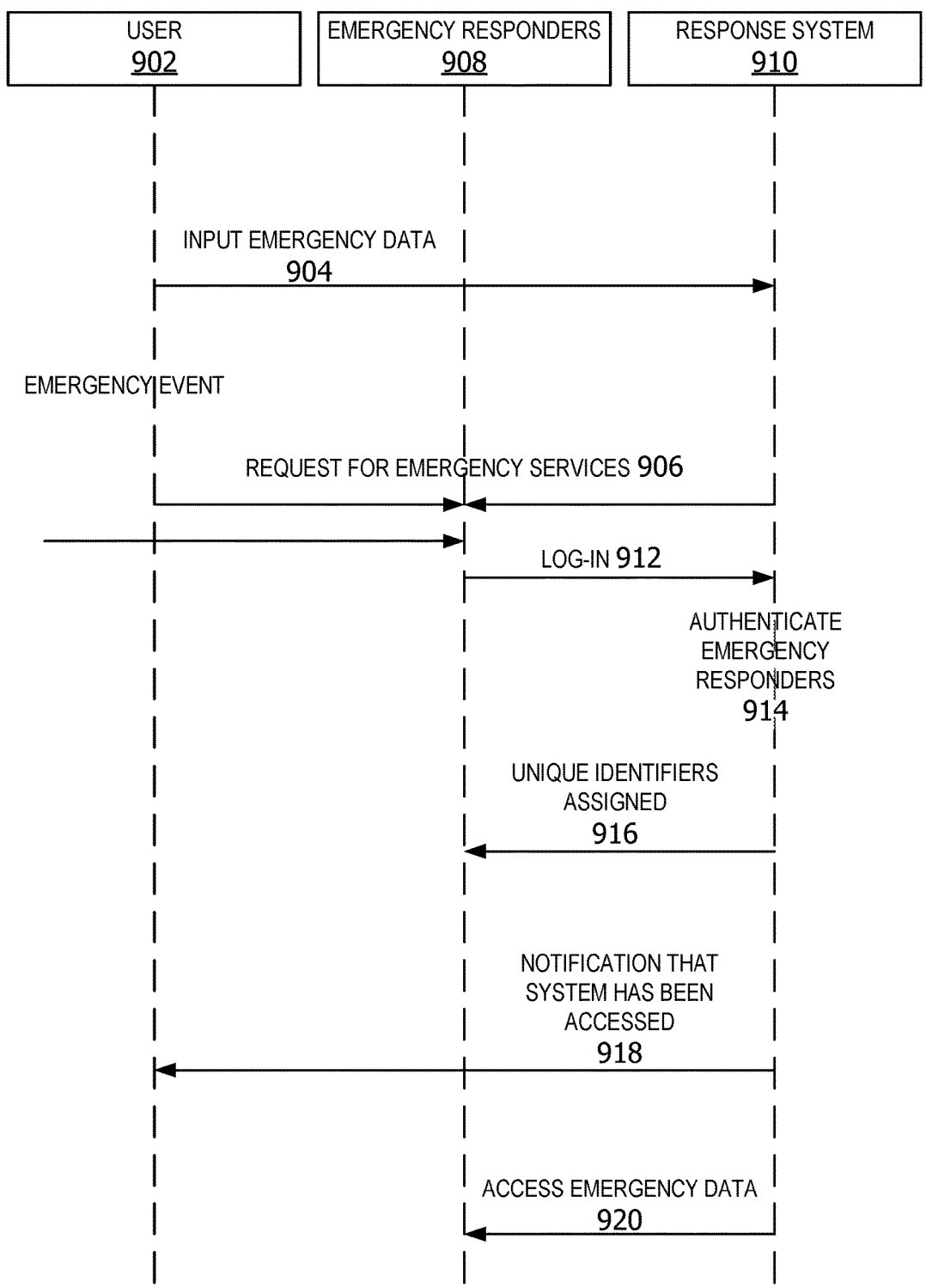
FIG. 9 is an exemplary block diagram of advance alert data transmissions.

FIG. 9 is an exemplary block diagram of advance alert data transmissions. A user 902 input emergency data 904 into the server 910. An emergency responder 908 requests the emergency data for use in providing emergency services 906. The emergency responders log-in 912 to the advance alert system server 910. The server 910 authenticates the emergency responders 914. The server 910 assigns unique identifiers 916 to the emergency responders. The server 910 sends a notification that the system has been accessed 918. The emergency data is accessed 920 by the emergency responders.

FIG. 10 is an exemplary block diagram of a user data collection page. Page 1000 is a page for a user to input data associated with the user and members of the user's family to generate the emergency data. The page 1000 is a non-limiting example of a user profile or user data page for collecting emergency data and other user information. The input data may include fields for a name 1002 of the members of the household, address, phone number, levels of the home, number of pets, whether there is a basement, attic, or cellar, birthdates 1008, gender 1006, age 1010, phone 1012, email address 1014, license plate data 1016, medical conditions of members of the household, whether a user is a head of household (HOH) 1004, notes 1018, as well as other personal information. The page 1000 may also include a date the input data was first entered by the user and the date the input data was last updated. The user is encouraged to update the information regularly via the edit options 1020 features.

FIG. 11 is an exemplary block diagram of generating anonymous data from user provided data. A user provides user data 1102. The user provided data includes personal details and other identifying information such as, but not limited to, names, birthdates, ages, gender, and other identifying information for the user and members of the user's household. The advance alert system filters the user data 1102 to exclude specific, identifying information and generate anonymous data 1104 for output to emergency responders. The anonymous data is generalized information excluding names, birthdates and specific ages. The anonymous data in this example identifies users by gender, age ranges, and non-specific descriptors, such as head of household and youth.

Figure 12:
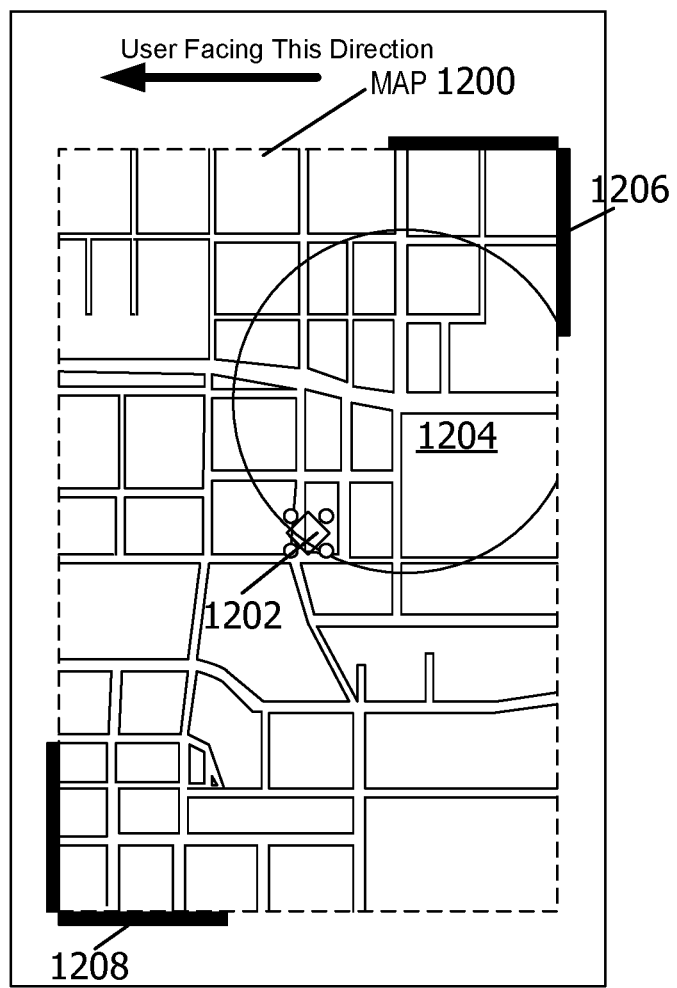
FIG. 12 is a map including an alert zone.

FIG. 12 is a map including an alert zone. The map 1200 is output to the subscriber with the notification alert. The map 1200 includes a current location of the subscriber 1202 within the alert zone 1204. The map 1200 in some examples includes an alert band 1206 and alert band 1208. The alert band 1206 may be a warning alert band indicating a red zone or danger zone towards the alert direction or a recommended direction alert band indicating a green zone or direction away from the alert location or a direction to move outside the alert zone. If the subscriber moves in the direction of the alert band 1208 indicator toward the green zone the user moves away from the potential danger and towards a potentially safer location.

In this example, the map 1200 includes both alert band 1206 and alert band 1208. In other examples, the map may include only a single alert band. The single alert band may be a warning alert band or a recommended direction alert band.

Figure 13:
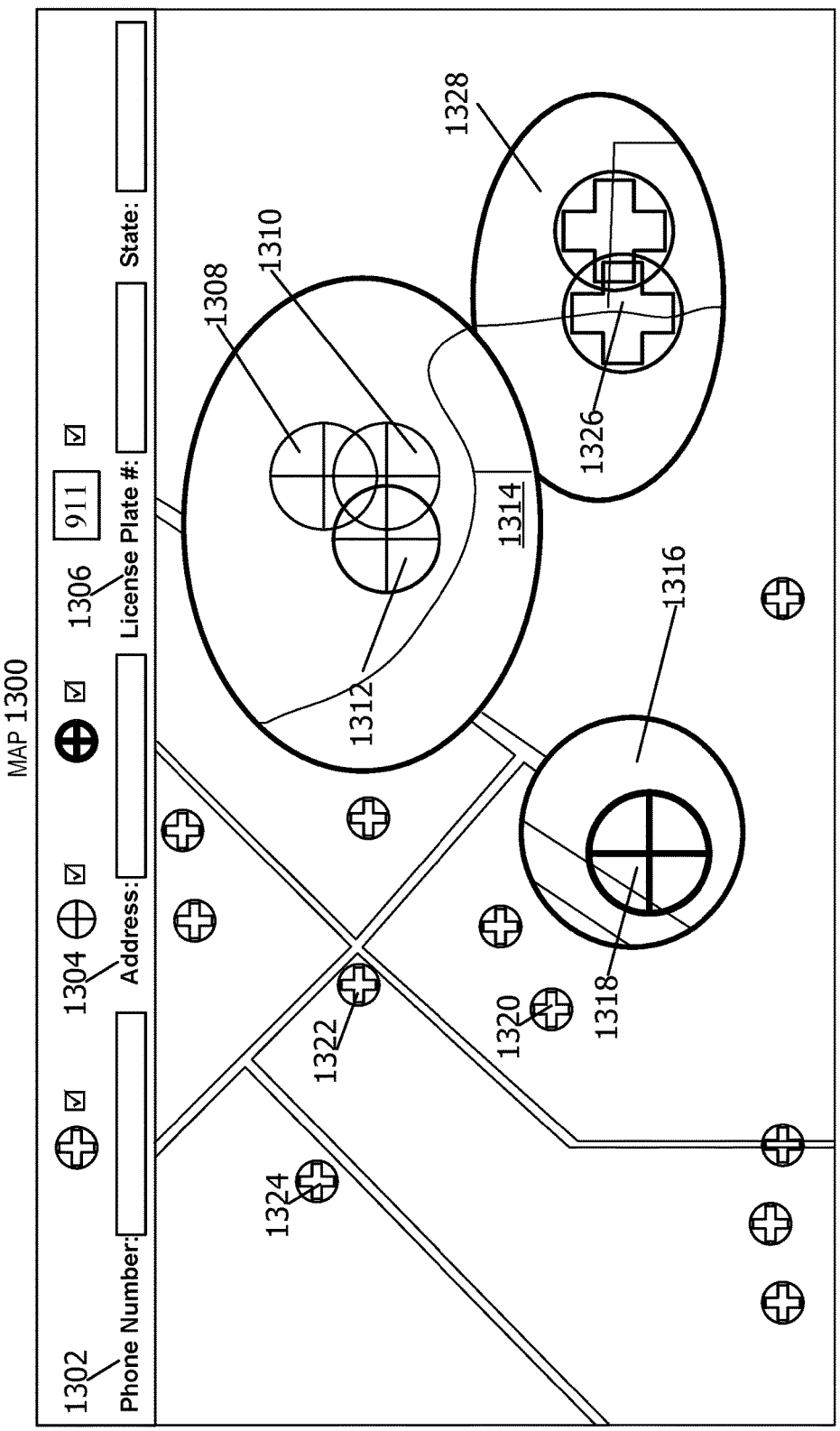
FIG. 13 is a map including subscriber locations and alert zones.

FIG. 13 is a map including subscriber locations and alert zones. Map 1300 is a map including locations of subscribers and current alert zones. The map feature enables a user to search for a particular user location based on phone number 1302, address 1304, license plate 1306, or other search fields.

The alert zones include indicators indicating a current threat level for each alert zone. In this example, alert zones 1308, 1310, and 1312 are alert zones at a perceived threat level or yellow alert level shown in a magnified area 1314. The alert zone 1318 is at an imminent threat level or red alert level, as shown in magnified area 1316.

The map in some examples shows the locations of other subscribers, such as subscribers 1320, 1322, and 1324. Another subscriber 1326 is shown in magnified area 1328. The map may be output to subscribers and/or emergency responders.

Figure 14:
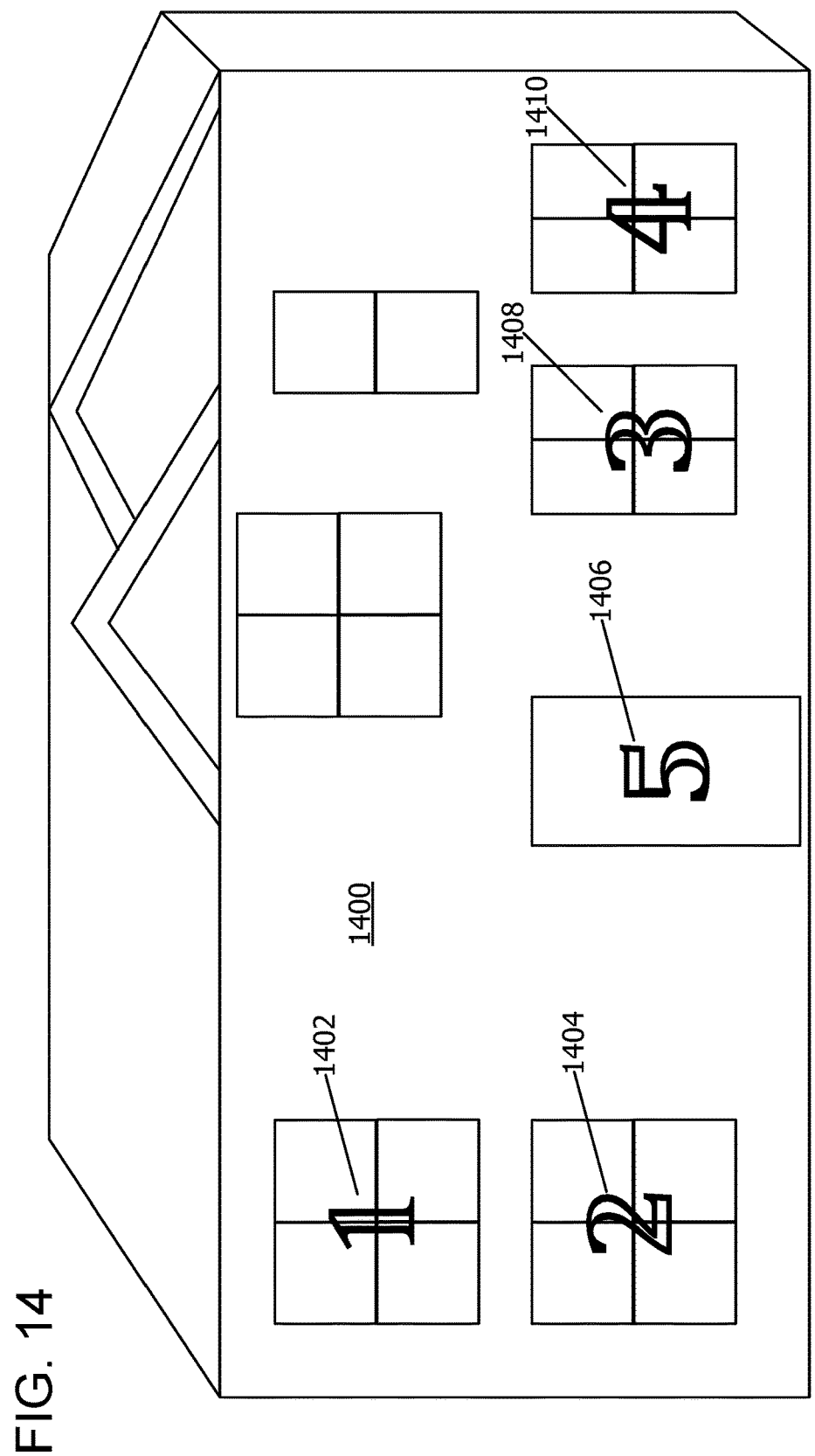
FIG. 14 is an image of a structure including an overlay of feature markers.

FIG. 14 is an image of a structure including an overlay of feature markers. In some examples, the emergency data for a user includes a set of images of a structure. The structure may include a house, apartment, dormitory, duplex, town house, office building, factory, garage, storage building, workshop, or any other type of residence. The set of images includes one or more pictures of an exterior of the structure taken from different directions, elevations, or vantage points. For example, the set of images may include an image of a front of a structure, a back of a structure, a right side of the structure, a left side of the structure, a driveway or parking lot associated with the structure, as well as any other features of potential interest to emergency responders.

In this non-limiting example, image 1400 is an image of a front side of a house. The image 1400 is includes a set of markers overlaying the image of the structure. In this example, the set of markers includes markers 1402, 1404, 1406, 1408, and 1410. However, the examples are not limited to five markers. An image of a structure included in the emergency data may include a single marker, as well as two or more markers.

A marker indicates a feature of potential interest to emergency responders. In some non-limiting examples, the markers identify features such as an occupant associated with a bedroom, office, or other portion of the structure, a handicapped occupant associated with that portion of the structure, an accessible entry and exit point, an inaccessible entry and exit point, geographic features, a fire escape or other exterior ladder or stairs leading to an upper level, a flammable substance storage location, a flammable substance storage location, or other hazardous condition. A flammable substance may include a can of gasoline stored in a garage, an oxygen tank stored in a bedroom, a propane tank, or any other type of flammable gas or liquid.

In this example, an elevation view of a front of a house is shown. A marker 1402 indicates an upstairs bedroom occupied by a resident of the home. The markers 1404, 1408, and 1410 indicate downstairs windows. The marker 1406 indicates an accessible entry or exit point for the first level of the house. In some examples, multiple windows having the same marker indicate a room having more than one window associated with the same room.

The images with markers may provide useful information to emergency responders. The markers on the map enable responders to determine which rooms are occupied, the location of potentially hazardous substances that may prove dangerous for responders, as well as other information useful for responders.

In this example, the markers 1402-1410 are shown as numbers overlaying an image of a front of a house. The markers are not limited to implementation as numbers. In other example, the markers are implemented as words, alphanumeric patterns, symbols, icons, flag symbols, or any other type of marker. For example, a marker identifying a portion of a house occupied by a handicapped resident may be a handicap symbol. In this example, the image of the structure includes an overlay of a handicap symbol on the window or other exterior portion of the house associated with the handicapped resident of the house.

In still other examples, a marker identifying flammable substances may be implemented as a fire symbol, a hazard symbol, a caution symbol, an image of a flame, a red color flag, a red "x" letter, the word "danger", or any other marker to indicate the flammable substances and potential hazard.

In another example, the set of images may include an image of a guide dog belonging to a blind resident. In the event of an emergency, such as a fire, emergency responders are able to access the emergency data including the images of the guard dog. The emergency data enables the firefighters to be aware of the disability of the resident, as well obtain images of the guide dog and the dog's name prior to entering the building to assist with the emergency. This information may assist the responders in locating and assisting the residents of the building during the emergency.

In another example, a marker on an image may be linked to additional information in the user's profile and/or database. For example, the marker 1402 may be clicked or selected to obtain information indicating the room is usually occupied by a male youth or child. The In one example, the advance alert system prompts a user to upload the set of images of a structure, such as a house, into the emergency data for the user profile stored on the data storage. Once loaded into their profile, the user labels, tags, or otherwise identifies which windows, doors, and features of the structure related to different members of the household as listed in the database. This eliminates the risk of utilizing an identifier, such as a sticker, on the exterior of the house which would be viewable to the public.

The markers overlaying the images are visible to emergency responders on a display displaying the emergency data. The markers identifying bedrooms, doorways, handicapped occupants, and other personal information are not visible externally on the actual, physical structure. In other words, a passerby looking at the actual house does not see the markers. Only an emergency responder viewing the emergency data sees the markers overlaying images of the house. This provides additional security for user information and protects user privacy. Moreover, the images and corresponding markers provide time-saving information to responders.

Figure 15:
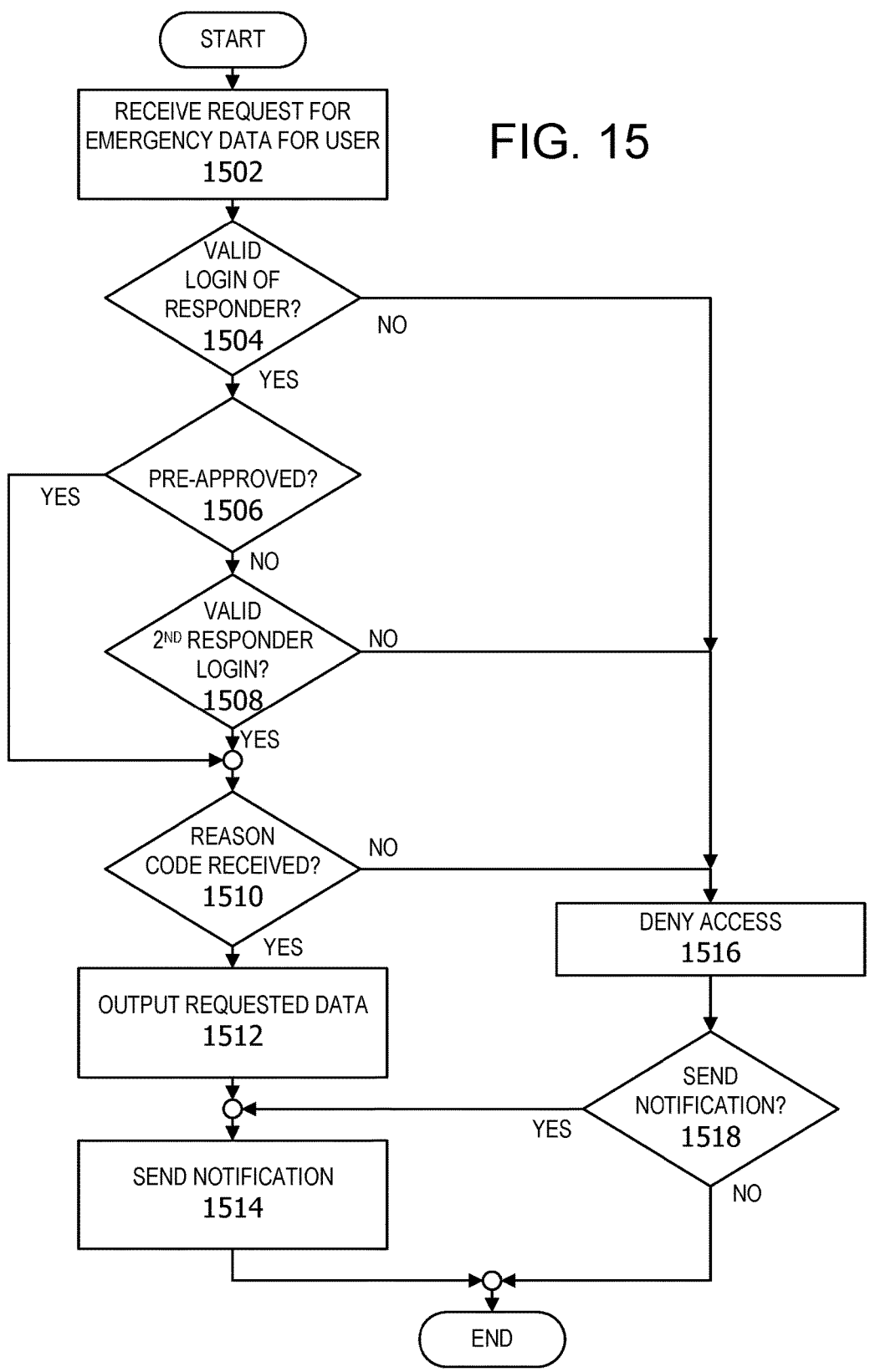
FIG. 15 is an exemplary flow chart illustrating operation of the advance alert server to provide emergency data to authorized emergency responders.

FIG. 15 is an exemplary flow chart illustrating operation of the map advance alert server to provide emergency data to authorized emergency responders. The process shown in FIG. 15 may be implemented by a computing device, such as, but without limitation, server 102 in FIG. 1 or server 200 in FIG. 2.

The process receives a request for emergency data associated with a user at 1502. The process determines whether a valid login of a responder is received at 1504. If a valid login is received, the process determines whether the responder is pre-approved at 1506. If no, the process determines whether a second responder login is valid at 1508. If yes, the process determines if a reason code is received at 1510. If yes, the process outputs the requested data at 1512. The process sends a notification of the data access at 1514. The notification may be sent to the user or to a supervisor of the responder. The process terminates thereafter.

Returning to operation 1504, if the login of the responder is not valid, the process denies access to the data at 1516. The process determines whether to notify the user of the denied access request at 1518. If yes, a notification is sent at 1514. The process terminates thereafter. In this example, the determination as to whether to notify the user of the denied access request may be made based on user preferences or other user settings in a user profile. For example, a user may wish to be notified of all access attempts or a user may only wish to be notified if the user's data is actually accessed.

Returning to 1508, if the second responder login is not valid, the process denies access to the data at 1516. The process determines whether to notify the user of the denied access request at 1518. If yes, a notification is sent at 1514. The process terminates thereafter.

Returning to 1510, if a reason code is not received at 1510, the process denies access to the data at 1516. The process determines whether to notify the user of the denied access request at 1518. If yes, a notification is sent at 1514. The process terminates thereafter. In some examples, access to the data is denied if the reason code is not a pre-approved or valid reason code. Some non-limiting examples of a valid reason code may include a 911 call, a car accident, or a house fire. A non-limiting example of an invalid reason code may include a traffic stop, a fire drill, a minor injury, or other non-urgent care situation.

While the operations illustrated in FIG. 15 are described as being performed by a server, aspects of the disclosure contemplate that performance of the operations by other entities. For example, a cloud service may perform one or more of the operations.

Figure 16:
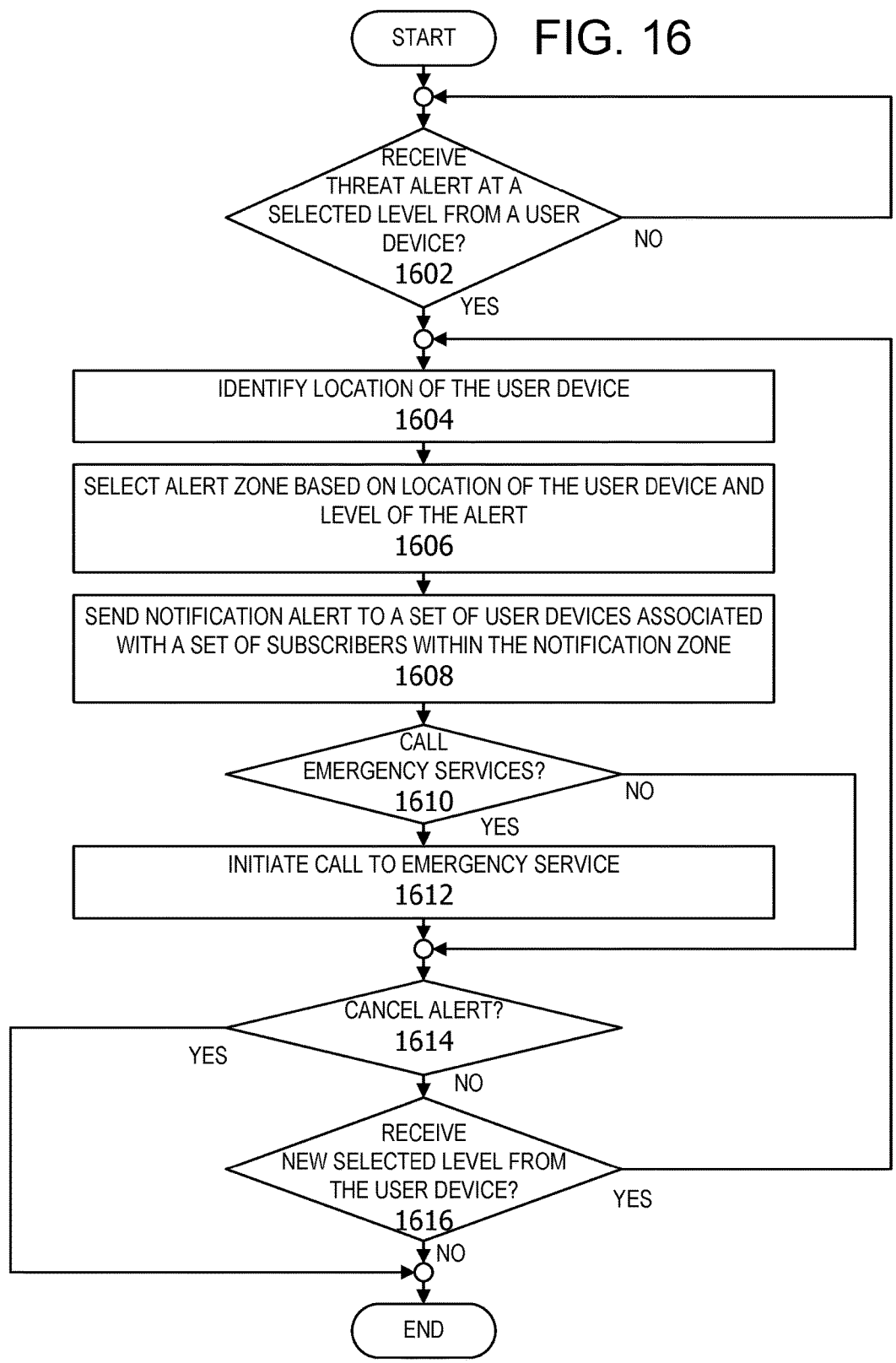
FIG. 16 is an exemplary flow chart illustrating operation of an advance alert server to respond received threat alerts.

FIG. 16 is an exemplary flow chart illustrating operation of an advance alert server to respond received threat alerts. The process shown in FIG. 16 may be implemented by a computing device, such as, but without limitation, server 102 in FIG. 1 or server 200 in FIG. 2.

The process determines whether a threat alert at a selected alert level is received from a user at 1602. If no, the process returns to 1602 until a threat alert is received. When a threat alert is received at 1602, the process identifies a location of the user device sending the threat alert at 1604. The process selects an alert zone based on the location of the user device and the level of the threat alert at 1606.

The process determines whether to call emergency services at 1610. If yes, the process initiates a call to emergency services at 1612. The process determines whether to cancel the alert at 1614. The process in some examples cancels the alert if a user or emergency responder selects to cancel the alert. If the alert is cancelled at 1614 the process terminates thereafter.

If the alert is not canceled at 1614, the process determines whether a new selected alert level is received from the user device at 1616. If yes, the process returns to 1604 and identifies the current location of the user device at 1604. The process iteratively executes operations 1604 through 1616 until no additional alerts are received or until the alert is canceled at 1614. The process terminates thereafter.

While the operations illustrated in FIG. 16 are described as being performed by a server, aspects of the disclosure contemplate that performance of the operations by other entities. For example, a cloud service may perform one or more of the operations.

Figure 17:
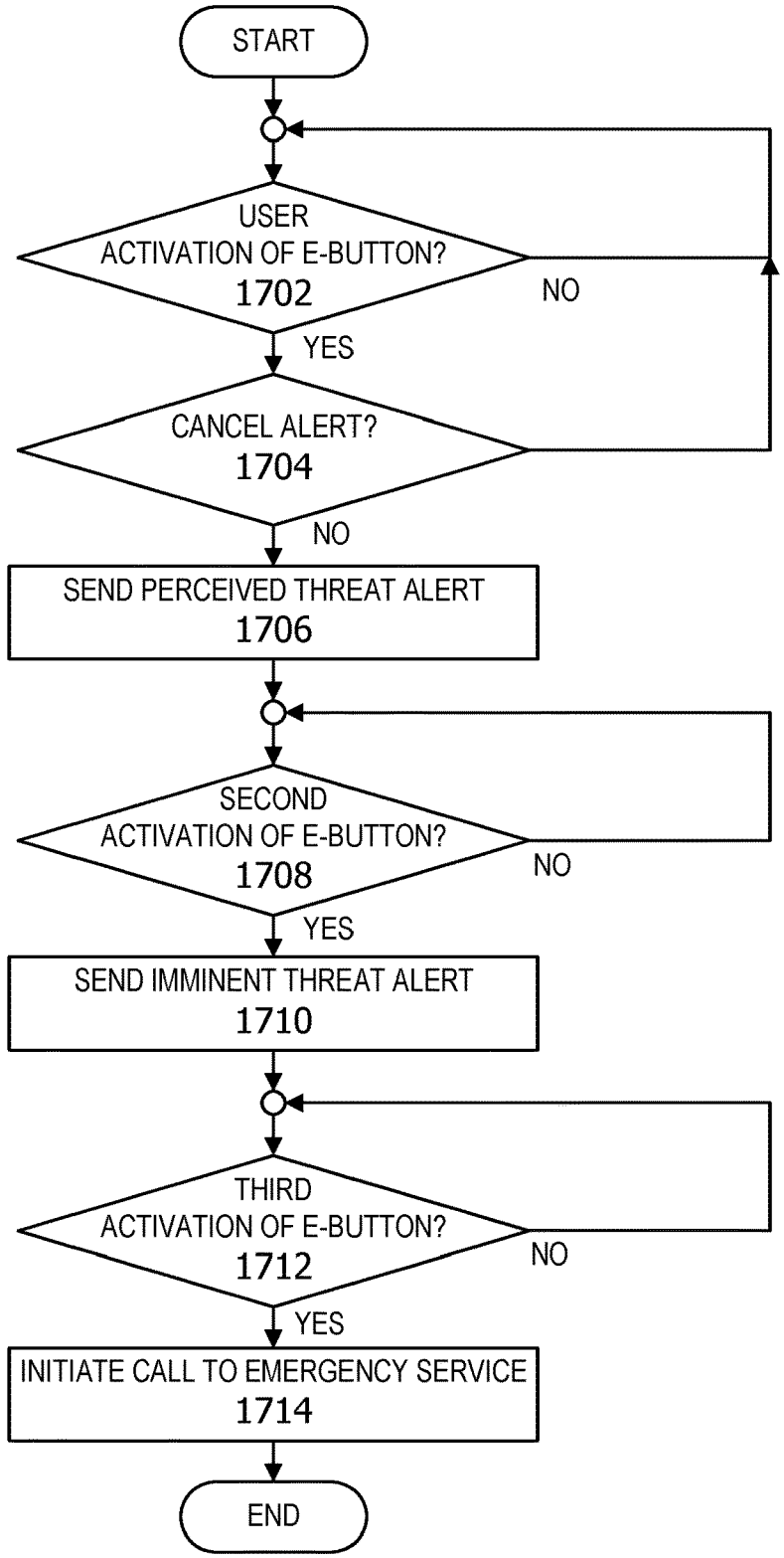
FIG. 17 is an exemplary flow chart illustrating operation of an e-button to send threat alerts to an advance alert server.

FIG. 17 is an exemplary flow chart illustrating operation of an e-button to send threat alerts to an advance alert server. The process shown in FIG. 17 may be implemented by a computing device, such as, but without limitation, an e-button device in the set of e-button devices 110 in FIG. 1, user device 204 in FIG. 2, user device 300 in FIG. 3, or e-button device 400 in FIG. 4.

The process detects a user activation of e-button at 1702. The process determines whether to cancel the alert at 1704. If yes, the process returns to 1702. If the alert is not cancelled, the process sends a perceived threat alert at 1706. The process determines whether a second activation of the e-button is detected at 1708. If no, the process returns to 1708. If a second activation is detected, the process sends an imminent threat alert at 1710. The process determines if a third activation of the e-button is detected at 1712. If no, the process returns to 1712. If a third activation of the e-button is detected at 1712, the process initiates a call to emergency services at 1714. The process terminates thereafter.

While the operations illustrated in FIG. 17 are described as being performed by a server, aspects of the disclosure contemplate that performance of the operations by other entities. For example, a cloud service may perform one or more of the operations.

Figure 18:
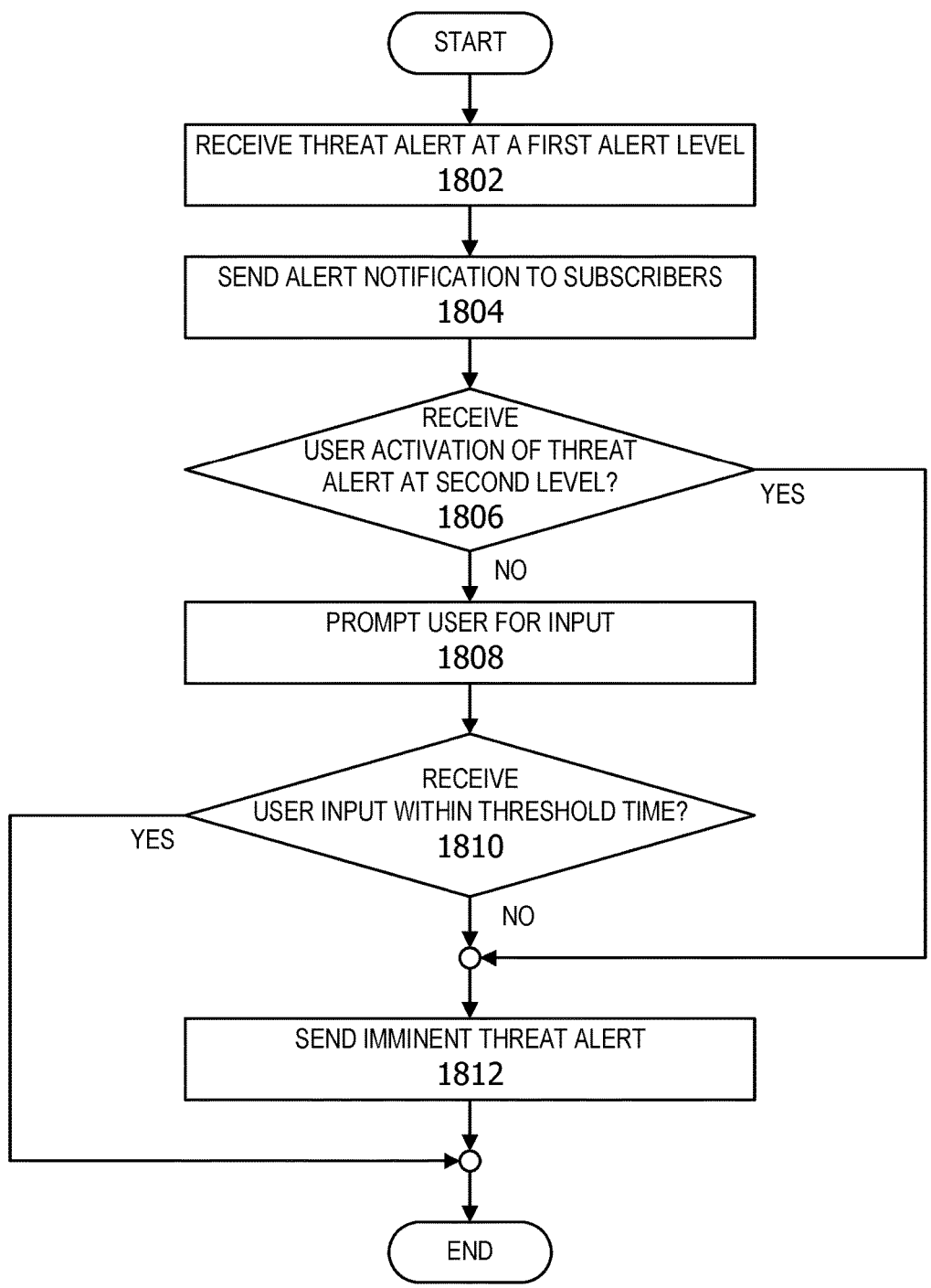
FIG. 18 is an exemplary flow chart illustrating operation of the advance alert server to send alert notifications to a set of subscribers.

FIG. 18 is an exemplary flow chart illustrating operation of the advance alert server to send alert notifications to a set of subscribers. The process shown in FIG. 18 may be implemented by a computing device, such as, but without limitation, server 102 in FIG. 1 or server 200 in FIG. 2.

The process receives a threat alert at a first level at 1802. The process sends an alert notification to one or more subscribers at 1804. The process determines whether user activation of a threat alert at a second level is received at 1806. If no, the process prompts the user for input at 1808. The process determines whether the user input is received within a threshold time at 1810, the process terminates thereafter.

If user activation of the threat alert at the second level is received at 1806, the process sends an imminent threat notification alert at 1812. The process terminates thereafter.

Returning to 1810, if user input is not received within the threshold time, the process sends an imminent threat alert at 1812. Sending the imminent threat alert in some examples includes calling emergency services, such as calling 911 or other appropriate emergency responder system.

While the operations illustrated in FIG. 18 are described as being performed by a server, aspects of the disclosure contemplate that performance of the operations by other entities. For example, one or more of the operations may be performed by a user device, such as a user device in the set of user devices 108, user device 204 in FIG. 2, user device 300 in FIG. 3, or e-button device 400 in FIG. 4. In other examples, a cloud service may perform one or more of the operations.

Figure 19:
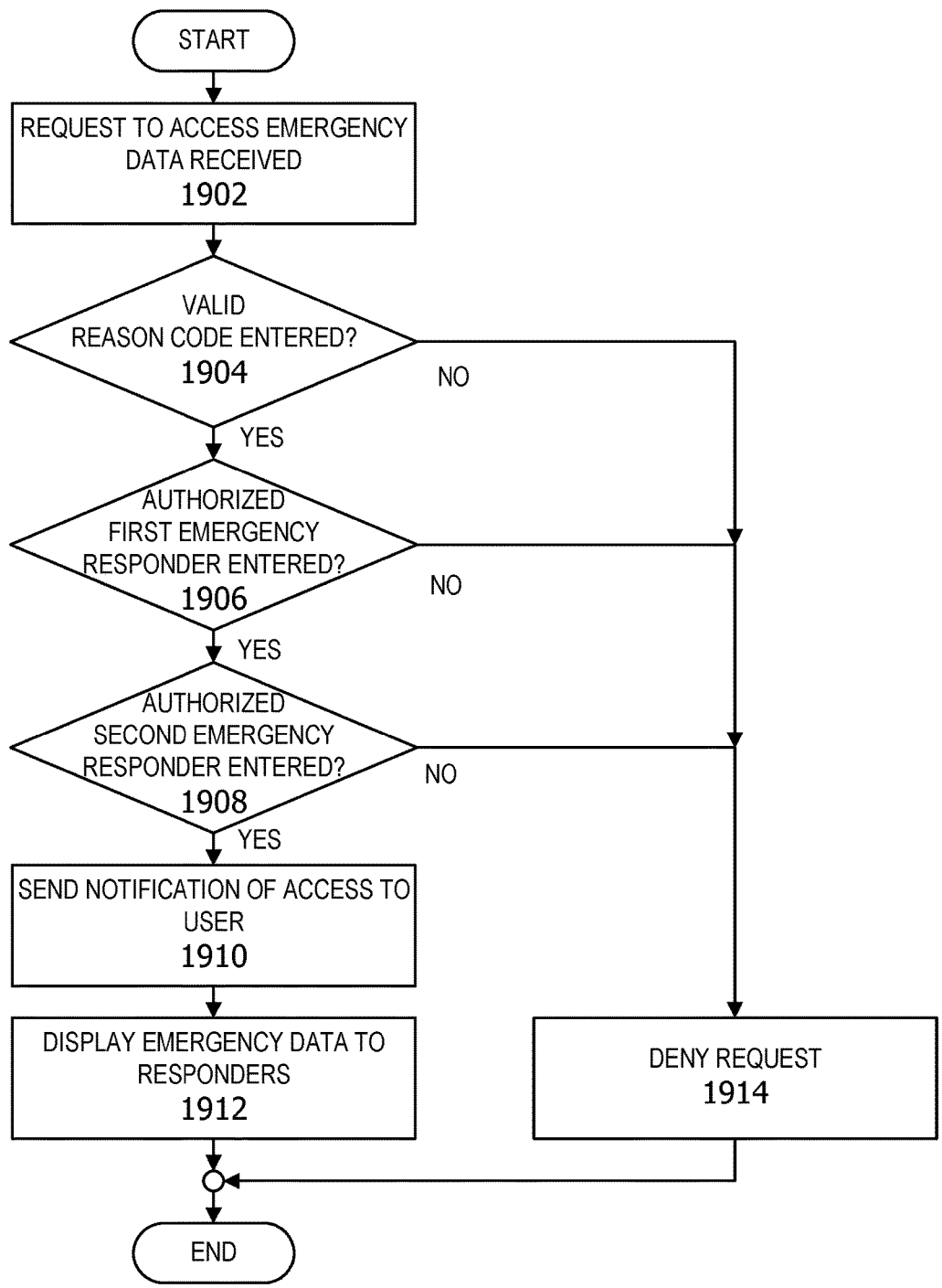
FIG. 19 is an exemplary flow chart illustrating operation of the advance alert server to provide emergency data to one or more emergency responders.

FIG. 19 is an exemplary flow chart illustrating operation of the advance alert server to provide emergency data to one or more emergency responders. The process shown in FIG. 19 may be implemented by a computing device, such as, but without limitation, server 102 in FIG. 1 or server 200 in FIG. 2.

The process receives a request to access emergency data at 1902. The process determines if a valid reason code is received at 1904. If yes, the process determines whether an authorized first emergency responder is entered at 1906. If yes, the process determines if a second authorized emergency responder is entered at 1908. If yes, the process sends the notification of access to a user at 1910. The user is the user associated with the emergency data. The process displays the emergency data to the one or more emergency responders at 1912. The process terminates thereafter.

Returning to 1904, if a valid reason code is not entered at 1904 or if the reason code is invalid, the process denies the request at 1914. The process terminates thereafter.

Returning to 1906, if an authorized first emergency responder is not entered at 1904 or if the emergency responder is unauthorized, the process denies the request at 1914. The process terminates thereafter.

Returning to 1908, if an authorized second emergency responder is not entered at 1904 or if the second emergency responder is unauthorized, the process denies the request at 1914. The process terminates thereafter.

While the operations illustrated in FIG. 19 are described as being performed by a server, aspects of the disclosure contemplate that performance of the operations by other entities. For example, one or more of the operations may be performed by a user device, such as a user device in the set of user devices 108, user device 204 in FIG. 2, user device 300 in FIG. 3, or e-button device 400 in FIG. 4. In other examples, a cloud service may perform one or more of the operations.

Figure 20:
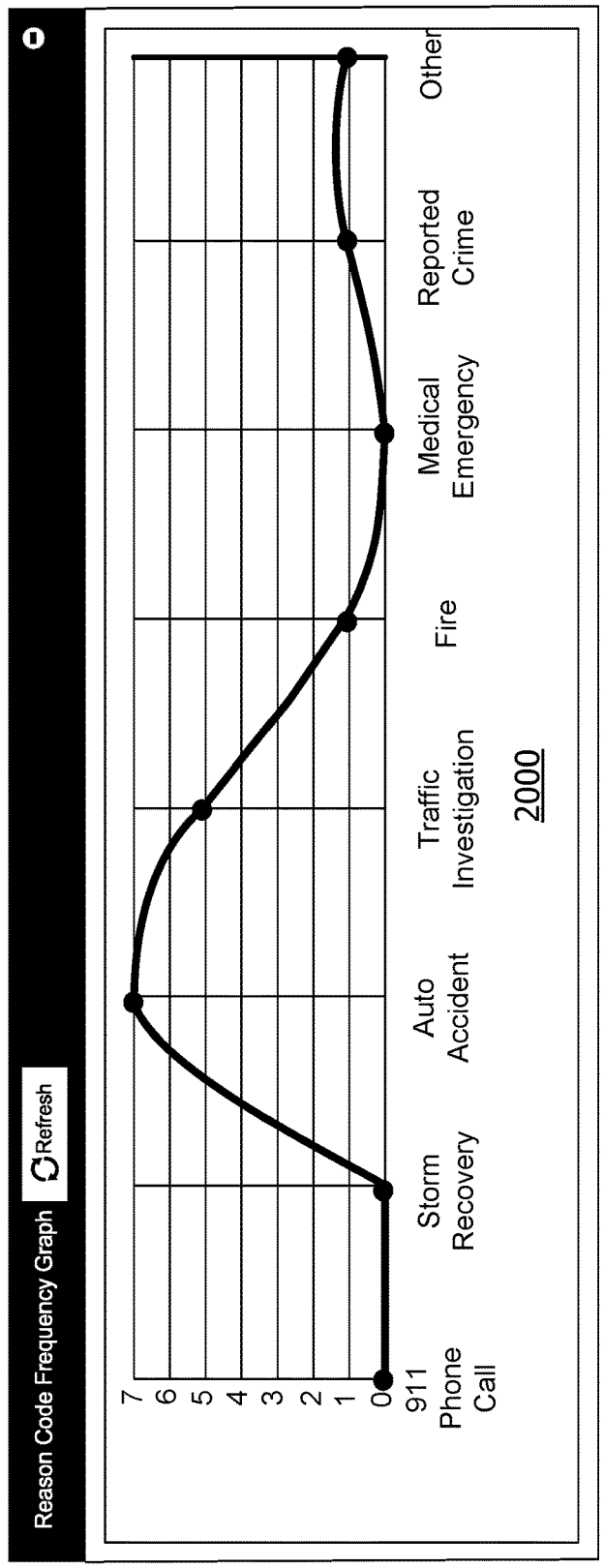
FIG. 20 is a graph illustrating reason code frequency.

FIG. 20 is a graph illustrating reason code frequency. In this example, the advance alert system maintains a data access history, such as the data access history 520 shown in FIG. 5 above. The data access history includes an identifier of each emergency responder accessing the user's emergency data, the reason code associated with the access, and the date and time of the access. This data access history for one or more users may be analyzed and output on a graph, such as graph 2000.

Graph 2000 is a reason code frequency graph showing reason codes and frequency of use of the reason codes by responders accessing user emergency data. In this non-limiting example, 911 calls, storm recovery, auto accidents, traffic investigations, fire, medical emergencies, reported crimes, and other reasons.

In the non-limiting example shown in FIG. 20, the reason code most frequently entered by responders accessing emergency data is an auto accident. The second most frequent reason code is traffic investigation. However, the examples are not limited to the reason codes shown in FIG. 20 or the frequency of use of the reason codes shown. In other examples, 911 calls or medical emergencies may be the most frequently used reason codes. In still other examples, fire or crime related reason codes may be used more frequently.

Other data which may be included in the data access history may include, without limitation, number of responders viewing the data, time interval between data accesses, number of attempted accesses, identification of data accessed, as well as any other data related to emergency data accesses by emergency responders.

Additional Examples

In some examples, the advance alert system provides a multi-stage advance alert to one or more subscribers and emergency responders within a selected alert zone. The advance alert system enables a user to select various levels of perceived threat in an escalating sequence resulting in a set of subscribers within a selected alert zone being notified or alerted at levels relative to the perceived threat. The alert notification provided to subscribers provided to subscribers within the selected alert zone allows the notified users to increase their awareness, proceed with greater caution, or otherwise respond in a manner they feel is appropriate. The alert notifications provide users with knowledge or warning of potentially dangerous or problematic situations in advance, before they would otherwise be aware of it.

Providing sensitive populations with access to emergency care is important because timely and effective interventions may make the different between life and death. However, the infrequent necessities of these interventions are balanced with the individual desire for privacy generally, and specifically preventing access of sensitive information by a third party intent on doing harm.

Moreover, providing emergency care to personnel at a place of work may present additional difficulties and administrative problems wherein an employer is unaware of unique medical challenges faced by one or more employees. Individual employees may be reluctant to share their medical information with their employers for a variety of reasons. The advance alert system collects and stores the employee or other user's information in a safe, secure manner until it is requested by authorized emergency responders. In addition, the emergency data provided to the responders in some examples is anonymous data excluding personally identifiable information, to further protect the privacy of users.

At least a portion of the functionality of the various elements in FIG. 1 and FIG. 2 may be performed by other elements in FIG. 1 and FIG. 2, or an entity (e.g., processor, web service, server, application program, computing device, etc.) not shown in FIG. 1 and FIG. 2.

In some examples, the operations illustrated in FIG. 15, FIG. 16, FIG. 17, FIG. 18, and FIG. 19 may be implemented as software instructions encoded on a computer readable medium, in hardware programmed or designed to perform the operations, or both. For example, aspects of the disclosure may be implemented as a system on a chip or other circuitry including a plurality of interconnected, electrically conductive elements.

While the aspects of the disclosure have been described in terms of various examples with their associated operations, a person skilled in the art would appreciate that a combination of operations from any number of different examples is also within scope of the aspects of the disclosure.

The term "Wi-Fi" as used herein refers, in some examples, to a wireless local area network using high frequency radio signals for the transmission of data. The term "BLUETOOTH" as used herein refers, in some examples, to a wireless technology standard for exchanging data over short distances using short wavelength radio transmission. The term "cellular" as used herein refers, in some examples, to a wireless communication system using short-range radio stations that, when joined together, enable the transmission of data over a wide geographic area.

While no personally identifiable information is tracked by aspects of the disclosure, examples have been described with reference to data monitored and/or collected from the users. In some examples, notice may be provided to the users of the collection of the data (e.g., via a dialog box or preference setting) and users are given the opportunity to give or deny consent for the monitoring and/or collection. The consent may take the form of opt-in consent or opt-out consent.

Exemplary Operating Environment

Exemplary computer readable media include flash memory drives, digital versatile discs (DVDs), compact discs (CDs), floppy disks, and tape cassettes. By way of example and not limitation, computer readable media comprise computer storage media and communication media. Computer storage media include volatile and nonvolatile, removable and non-removable media implemented in any method or technology for storage of information such as computer readable instructions, data structures, program modules or the like. Computer storage media are tangible and mutually exclusive to communication media. Computer storage media are implemented in hardware and exclude carrier waves and propagated signals. Computer storage media for purposes of this disclosure are not signals per se. Exemplary computer storage media include hard disks, flash drives, and other solid-state memory. In contrast, communication media typically embody computer readable instructions, data structures, program modules, or the like in a modulated data signal such as a carrier wave or other transport mechanism and include any information delivery media.

Although described in connection with an exemplary computing system environment, examples of the disclosure are capable of implementation with numerous other general purpose or special purpose computing system environments, configurations, or devices.

Examples of well-known computing systems, environments, and/or configurations that may be suitable for use with aspects of the disclosure include, but are not limited to, mobile computing devices, personal computers, server computers, hand-held or laptop devices, multiprocessor systems, gaming consoles, microprocessor-based systems, set top boxes, programmable consumer electronics, mobile telephones, mobile computing and/or communication devices in wearable or accessory form factors (e.g., watches, glasses, headsets, bracelets, wristbands, key chains, or earphones), network PCs, minicomputers, mainframe computers, distributed computing environments that include any of the above systems or devices, and the like. Such systems or devices may accept input from the user in any way, including from input devices such as a keyboard or pointing device, via gesture input, proximity input (such as by hovering), and/or via voice input.

Examples of the disclosure may be described in the general context of computer-executable instructions, such as program modules, executed by one or more computers or other devices in software, firmware, hardware, or a combination thereof. The computer-executable instructions may be organized into one or more computer-executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other examples of the disclosure may include different computer-executable instructions or components having more or less functionality than illustrated and described herein.

In examples involving a general-purpose computer, aspects of the disclosure transform the general-purpose computer into a special-purpose computing device when configured to execute the instructions described herein.

The examples illustrated and described herein as well as examples not specifically described herein but within the scope of aspects of the disclosure constitute exemplary means for providing advance alerts and emergency data to users, such as, but not limited to, subscribers and emergency responders. For example, the elements illustrated in FIG. 1 and FIG. 2, such as when encoded to perform the operations illustrated in FIG. 15, FIG. 16, FIG. 17, FIG. 18, and FIG. 19, constitute exemplary means for receiving a request from a first emergency responder to access at least a portion of emergency data associated with a user; exemplary means for determining whether a first emergency responder is pre-authorized; outputting the requested emergency data to the pre-authorized first emergency responder; requesting a second login from a second emergency responder on determining the first emergency responder is an authorized responder lacking pre-approval; exemplary means for denying access to the emergency data on failing to receive a valid second login from the second emergency responder; exemplary means for outputting the requested emergency data to the second responder on receiving the valid second login from the second emergency responder.

In another example, the elements illustrated in FIG. 1 and FIG. 2, such as when encoded to perform the operations illustrated in FIG. 15, FIG. 16, FIG. 17, FIG. 18, and FIG. 19, constitute exemplary means for receiving a threat alert comprising a user selected alert level from at least one user device via a network; exemplary means for identifying a current location of the at least one user device; exemplary means for selecting an alert zone comprising an area including the current location of the at least one user device; and exemplary means for sending a notification alert to a set of user devices currently located within the alert zone.

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of" The phrase "one or more of the following: A, B, and C" means "at least one of A and/or at least one of B and/or at least one of C."

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. One or more computer storage media embodying computer-executable components, said components comprising:
   a data storage device storing emergency data provided by at least one user, the emergency data comprising data associated with the at least one user;
   an alert generation component that is executed to cause at least one processor to send a notification alert to a set of subscribers within an alert zone in response to receiving a threat alert from the at least one user within the alert zone;
   an authorization component that is executed by the at least one processor to cause the at least one processor to verify a unique identifier associated with a first emergency responder requesting access to at least a portion of the emergency data associated with the at least one user to determine if the first emergency responder is authorized to access the at least the portion of the emergency data, the authorization component requests a second login from a second emergency responder in response to receiving a valid first login from the first emergency responder, access to the at least the portion of the emergency data is denied on receiving an invalid second login from the second emergency responder and the at least the portion of the emergency data is output to a computing device associated with the first emergency responder on receiving a valid second login from the second emergency responder; and
   a response component that is executed by the at least one processor to cause the at least one processor to filter the emergency data provided by the at least one user to generate anonymized emergency data and send the at least the portion of the anonymized emergency data to the one or more emergency responders in response to determining the one or more emergency responders are authorized.

2. The computer storage media of claim 1, further comprising:
   a mapping component that is executed to cause the at least one processor to generate a map and output the map to a user device associated with at least one user, the map including a current location of the user, a representation of the alert zone, and a safe direction indicator away from the alert zone.

3. The computer storage media of claim 2, further comprising:
   a notification component that is executed to cause the at least one processor to send a notification of access to the emergency data by at least one emergency responder to the at least one user associated with the emergency data, the notification of access comprising a reason for the emergency data access.

4. The computer storage media of claim 3, further comprising:
   a mute alerts component that is executed to cause the at least one processor to stop sending of alerts to the set of subscribers within a mute alerts zone for a predetermined period of time in response to a request to mute alerts by an authorized emergency responder.

5. A system comprising:
   a processor;
   a memory, the memory storing one or more computer-executable components; and
   a data storage device, the data storage device storing emergency data provided by a user, the emergency data comprising data associated with the user, the one or more computer-executable component comprising:
      an authorization component that is executed by the at least one processor to cause the at least one processor to verify a first login associated with a first emergency responder requesting access to at least a portion of the emergency data associated with the user to determine if the first emergency responder is authorized to access the at least the portion of the emergency data, the authorization component requests a second login from a second emergency responder in response to receiving a valid first login from the first emergency responder, access to the at least the portion of the emergency data is denied on receiving an invalid second login from the second emergency responder; and
      a response component that is executed by the at least one processor to cause the at least one processor to filter the emergency data provided by the user to generate anonymized emergency data and send the at least the portion of the anonymized emergency data to a computing device associated with the first emergency responder in response to receiving a valid second login from the second emergency responder.

6. The system of claim 5, further comprising:
   a notification component that is executed by the at least one processor to cause the at least one processor to send a notification of access to the at least the portion of the anonymized emergency data by at least one emergency responder to a user device associated with the user, the notification of access comprising a reason for the emergency data access.

7. The system of claim 5, further comprising:
   a notification component that is executed by the at least one processor to cause the at least one processor to send a notification of access to the at least the portion of the anonymized emergency data by at least one emergency responder to a user device associated with a supervisor of the first emergency responder.

8. The system of claim 5, further comprising:
   a notification component that is executed by the at least one processor to cause the at least one processor to send a notification of access to the at least the portion of the anonymized emergency data by at least one emergency responder to a user device associated with a designated emergency contact person of the user.

9. The system of claim 5, further comprising:
   an alert generation component that is executed to cause at least one processor to send a notification alert to a set of subscribers within an alert zone in response to receiving a threat alert from the user within the alert zone;
   an analysis component, wherein the at least one processor executes the analysis component to cause the at least one processor to analyze a source of the threat alert and a speed associated with the user device sending the threat alert, wherein the analysis component identifies a radius of the alert zone from the source of the threat alert; and a mapping component that is executed to cause the at least one processor to output the map to a user device associated with the user, the map including a representation of the alert zone and a safe direction indicator away from the alert zone.

10. The system of claim 5, further comprising:

the authorization component that is executed by the at least one processor to cause the at least one processor to request a reason code from the first emergency responder requesting access to the at least the portion of the emergency data, wherein the at least the portion of the anonymized emergency data is output to the first emergency responder on determining a valid reason code for the request is received, and wherein access to the at least the portion of the anonymized emergency data is denied on determining the valid reason code is not received from the first emergency responder.

11. A method comprising:

storing, in a data storage device, emergency data provided by a user, the emergency data comprising data associated with the user;

verifying, by an authorization component, a first login received from a first computing device associated with a first emergency responder requesting access to at least a portion of the emergency data associated with the user to determine whether the first emergency responder is authorized to access the at least the portion of the emergency data;

requesting, by the authorization component, a second login from a second emergency responder in response to receiving a valid first login from the first emergency responder;

denying access to the at least the portion of the emergency data on receiving an invalid second login from the second computing device associated with a second emergency responder via a network;

filtering the emergency data provided by the user to generate anonymized emergency data; and sending the at least the portion of the anonymized emergency data to a computing device associated with the first emergency responder via the network in response to receiving a valid second login from the second emergency responder.

12. The method of claim 11, further comprising:

requesting, by the authorization component, a reason code from the first emergency responder requesting access to the at least the portion of the emergency data;

outputting the portion of the anonymized emergency data to the computing device associated with the first emergency responder on determining a valid reason code for the request is received; and denying access to the emergency data by the first emergency responder on determining the valid reason code is not received.

13. The method of claim 11, further comprising:

sending, by a notification component, a notification of access to the at least the portion of the emergency data, by the first emergency responder to the user, the notification comprising an identification of the first emergency responder and a reason for the emergency data access.

14. The method of claim 11, further comprising:

sending, by a notification component, a notification of access to the at least the portion of the emergency data, by the first emergency responder to a user device associated with a supervisor of the first emergency responder.

15. The method of claim 11, further comprising:

sending, by a notification component, a notification of access to the at least the portion of the emergency data, by the first emergency responder to a user device associated with a designated emergency contact of the user.

16. The method of claim 11, further comprising:

storing a data access history of emergency responder access to the emergency data associated with the user, the data access history comprising a date of each access of the emergency data and a reason for each access of the emergency data.

17. The method of claim 11, wherein the at least the portion of the anonymized emergency data includes a set of images of a structure overlaid with a set of markers, wherein a marker in the set of markers indicates a feature, the feature comprising at least one of an occupant associated with that portion of the structure, a handicapped occupant associated with that portion of the structure, an accessible entry and exit point, an inaccessible entry and exit point, or hazardous condition.

18. The method of claim 11, further comprising:

receiving a threat alert from a user device associated with the user;

on determining a threshold response time is reached without receiving additional input from the user device associated with the user following initiation of the threat alert, prompting the user to enter additional input; and on failing to receive the additional input from the user, automatically initiating a call to emergency services.

19. The method of claim 11, further comprising:

an alert generation component that is executed to cause at least one processor to send a notification alert to a set of subscribers within an alert zone in response to receiving a threat alert from the user within the alert zone;

an analysis component, wherein the at least one processor executes the analysis component to cause the at least one processor to analyze a source of the threat alert and a speed associated with the user device sending the threat alert, wherein the analysis component identifies a radius of the alert zone from the source of the threat alert; and a mapping component that is executed to cause the at least one processor to output the map to a user device associated with the user, the map including a representation of the alert zone and a safe direction indicator away from the alert zone.

20. The method of claim 11, further comprising:

removing identifying information from the emergency data to generate anonymized emergency data.

* * * * *